(12) United States Patent
Gahunia et al.

(10) Patent No.: US 6,696,578 B2
(45) Date of Patent: Feb. 24, 2004

(54) DIFUROPYRONE DERIVATIVES

(75) Inventors: Harpal Kaur Gahunia, Warsaw, IN (US); Kenneth Pritzker, Toronto (CA); Reinhold Vieth, Toronto (CA)

(73) Assignee: Mount Sinai Hospital, Toronto (CA)

( * ) Notice: Subject to any disclaimer, the term of this patent is extended or adjusted under 35 U.S.C. 154(b) by 0 days.

(21) Appl. No.: 09/966,840

(22) Filed: Sep. 28, 2001

(65) Prior Publication Data

US 2002/0086333 A1 Jul. 4, 2002

Related U.S. Application Data

(63) Continuation of application No. PCT/CA00/00750, filed on Jun. 22, 2000.
(60) Provisional application No. 60/140,350, filed on Jun. 22, 1999.

(51) Int. Cl.$^7$ ............... C07D 493/14; C07K 16/22; A01N 43/26; G01N 33/53
(52) U.S. Cl. ............... 549/387; 435/7.5; 435/7.95; 530/389.1; 530/389.2; 514/455
(58) Field of Search .......................... 549/387

(56) References Cited

FOREIGN PATENT DOCUMENTS

| EP | 0 391 625 | 10/1990 |
|---|---|---|
| WO | WO92/16517 | 11/1992 |

OTHER PUBLICATIONS

Stockwell RA. Chondrocyle metabolism.. Biology of Cartilage Cells. (Ed) Harrison RJ. McMinn RMH. 1979:81–123.
Poole, AR, Cartilage in Health and Disease, in Arthritis and Allied Conditions. A Textbook of Rheumatology. 12th ed. McCarty D. Koopman W. editors. Malvern: Lea and Febiger, 1992, 279–333, 1986.
Israel et al, Oral Maxillofac Surg 49(7):708, 1991.
Robins, Biochem J. 207:617–620, 1992.
A. Ratcliffe, et al, J. Orthopaedic Research vol. 10, 350, 1992.
Boyle et al, Osteoarthritis and Cartilage, 1995, 3:117.
Kirkpatrick CA et al, Cell Tissue Res, 1982, 224:441–448.
Le Lous M. et al Calcif Tissue Int, 1981, 33:403–407.
Rabinovitz JL et al Clin Orthop 1979, 143:260–265.
Simpson TJ, Nat Prod Rep 1987, 4:339–376.
Staunton J., Wilkinson B. The Biosynthesis of alipathic polyketides. In Biosynthesis—Polyketides and vitamins. (ed) Leeper FJ and Vederas JC. Springer–Verlag Berlin Heidelberg, 1998; pp 49–92.
Robson P, et al, J. Biol Chem. 1993, 268:1440–1447.
Robson P et al, Comp Biochem Physiol 1978, 118B:71–78.
C. Colombo et al Arthritis and Rheumatism 26:875, 1983.
R. Holmdahl et al, Arthritis and Rheumatism 29:400, 1986.
D. Visco et al, Osteoarthritis and Cartilage 4–9, 1996.
MJ Bellmunt, et al, Lung 173:177–185, 1995.
A. Uchiyama et al, J Biochem 110:714–718, 1991.
P. Odetti et al: Lab Invest 70:61–67, 1994.
Hormel et al, Biochim Biophys Acta 1078:243–250, 1991.
H.K. Gahunia et al, J. Rheumat., 2002; 29(1), p 147.
H.K. Gahunia et al. J. Rheumat., 2002; 29(1), p. 154.
Thonar, E. J–MA et al, Acta Orthop Scand. (Suppl. 266) 1995; 66:103–106.
Witter J, Arthritis Rheum 30(5):519, 1987.
Walakovits, Arthritis Rheum 35(1):35–42, 1992.
M. Takahashi et al. Arthritis and Rheumatism 37(5):724–728, 1994.
K. Pritzker, Annals of the Rheumatic Diseases 53:406, 1994.
XP002150534, Henrio etal., Tetrahedron, vol. 33, pp. 191–197 (1977).
XP002150535, Grol, Tetrahedron, vol. 30, pp. 3621–3624 (1974).
XP002150536, Fischer et al., HoppeSeyler's Z. Physiol. Chem., vol. 267, pp. 201–206 (1941).

*Primary Examiner*—Mary E. Ceperley
(74) *Attorney, Agent, or Firm*—Merchant & Gould, P.C.

(57) ABSTRACT

A novel cartilage-specific compound and methods of diagnosis in medical and veterinary contexts using the compound. Screening methods for therapeutic substances and methods of treatment are also provided.

2 Claims, 3 Drawing Sheets

DIFUROPYRONE DERIVATIVES

This application is a continuation of international application number PCT/CA00/00750, filed Jun. 22, 2000, and claims benefit of U.S. provisional application No. 60/140, 350, filed Jun. 22, 1999.

FIELD OF THE INVENTION

The invention relates to a novel compound; to methods of diagnosis in medical and veterinary contexts using the compound; screening methods for therapeutic substances; and methods of treatment.

BACKGROUND OF THE INVENTION

Biochemical markers in body fluids are valuable tools in clinical medicine. Biochemical tests are relevant in such diseases as diabetes, myocardial infarction, and osteoporosis. The objective of a biochemical marker is to detect latent disease, or to monitor pre-existing disease and its treatment. To date, there has been no useful marker found that is relevant to the assessment of cartilage in arthritic conditions.

Cartilage matrix is made up of a complex mixture of components including collagen type II, collagen IX and collagen XI, procollagen molecules, proteoglycans, aggrecan, hyaluronic acid, link proteins, etc. Several cartilage components have been studied for their clinical utility. The C-propeptide of type II collagen, a marker of type II collagen synthesis, may reflect cartilage repair (Poole AR, Cartilage in Health and Disease, In: Arthritis and Alllied Conditions. A Textbook of Rheumatology. 12$^{th}$ ed. McCarty D. Koopman W, editors. Malvern: Lea and Febiger, 1992:279–333, 1986). Another component, aggrecan, is usually elevated in osteoarthritic joint fluid (Ratcliffe, J. Oral Maxillofac Surg 49(7):708, 1991; Witter J, Arthritis Rheum 30(5):519, 1987). Some catabolic enzymes, especially metalloproteases, are found in osteoarthritic joint fluid (Walakovits, Arthritis Rheum. 35(1):35–42, 1992).

Fluorescent markers associated with bone disease are released from collagen and its peptide fragments through acid hydrolysis, and are relatively stable in biological fluids. The two known types of fluorescent compounds within cartilage, pyridinium compounds and pentosidine have been studied in synovial fluid, urine, blood, and other biological fluids. Pyridinium compound levels were found to be essentially unchanged with age, or decreased slightly, and pentosidine increased with age (Takahashi M et al. Arthritis and Rheumatism 37(5):724–728, 1994). Pyridinium compounds can be measured in the urine, serum, or plasma as a ratio with creatinine. In bone disease, pyridinium compounds are increased with bone resorption. In osteoarthritis and rheumatoid arthritis patients, urinary pyridinium compounds are increased. However, Robins (Biochem J. 207:617–620, 1992) concluded that the cartilage itself contributed very little to the urinary rise in pyridinium compounds in these patients and the rise was attributed to bone resorption rather than cartilage degradation.

A molecule that is chemically stable, can be measured in biological fluids, and which is specific to cartilage is desirable as a biochemical marker to aid in the assessment of, and monitoring the treatment of osteoarthritis and other arthritic conditions.

SUMMARY OF THE INVENTION

The present inventors have identified a novel compound derived from, and found in cartilage, articular cartilage containing tissues such as intervertebral disc, trachea, and sternum, and cartilagenous metaplasia and neoplasia of tissues. The novel compound was also detected in the synovial fluids of human and calf. The compound is also found in cartilage cultured in vitro. Anatomically, the level of the compound increases with the cartilage depth, and in this respect it parallels the proteoglycan content.

The present inventors observed that levels of the compound decreased in the cartilage tissue with progression of osteoarthritis. Therefore, the compound can be used to evaluate cartilage injury and repair in patients with osteoarthritis.

The present invention therefore relates to a difuro-8-pyrone of the formula I

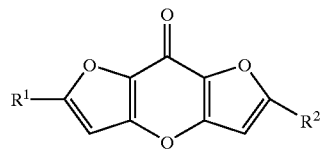

wherein $R^1$ and $R^2$ are the same or different and represent hydrogen, alkyl, alkenyl, alkynyl, alkoxy, hydroxyl, thiol, amino, halogen, carboxylic acid or esters or thioesters thereof, amide, azide, imide, imine, imidazole, acetal, nitrile, nitro, sulfate, sulfonic or sulfinic acid or esters thereof, phosphate or phosphonate acids or esters thereof, silyl, sulfoxide, sulfone, oxime, phosphonate, cycloalkyl, unsaturated monocyclic hydrocarbons, aryl, and aryloxy, and salts and optically active and racemic forms of a compound of the formula I.

In an embodiment of the invention, compounds of the formula I are provided wherein $R^1$ and $R^2$ are the same or different and represent $C_1$ to $C_6$ alkyl, preferably methyl, or ethyl. Most preferably the compound of the formula I of the invention is 2,6-dimethyl-difuro-8-pyrone (also referred to herein as "Cartilage Marker-1" or "CM-1").

The invention also comprises a crystal form of a compound of the invention, a precursor of a compound of the invention, and a polymer comprising a plurality of compounds of the invention.

Further, the present invention provides a method for preparing a compound of the formula I as defined herein, and a composition, preferably a pharmaceutical composition, comprising a compound of the formula I, a crystal form or precursor thereof, or a polymer of the invention as an active agent.

Still further, the present invention provides a method of detecting a compound of the invention in a sample, comprising the step of reacting the sample with a substance that binds to, or interacts with a compound of the invention. The substance may be an antibody, which recognizes a compound of the invention.

The invention also provides a method of diagnosis of a condition involving modifications in cartilage, articular cartilage containing tissues such as intervertebral disc, trachea, and sternum, and/or cartilagenous metaplasia and neoplasia of tissues in a subject comprising the step of subjecting a biological sample from the subject to a test for detection of a compound of the invention.

The invention also provides a method of monitoring progress of a condition involving modifications in cartilage, articular cartilage containing tissues such as intervertebral disc, trachea, and sternum, and/or cartilagenous metaplasia and neoplasia of tissues in a subject, or monitoring efficacy of treatment of such a condition, comprising periodically testing a sample from the subset for the presence of a compound of the invention.

The invention also provides a method of screening for putative therapeutic agents for the prevention and/or treatment of a condition involving modifications in cartilage, articular cartilage containing tissues such as intervertebral disc, trachea, and sternum, and/or cartilagenous metaplasia and neoplasia of tissues comprising testing the ability of the putative agents to bind to, interact with, inhibit, or stimulate a compound of the invention, or a precursor thereof. Also included are therapeutic agents identified using this method of screening.

The invention also features a method for delivering a substance to a tissue e.g. cartilage tissue, the method includes administering to a subject the substance linked to a compound of the invention. A molecular conjugate is also contemplated which includes a compound of the invention and an imaging or therapeutic agent.

The compound of the invention, and polymers thereof are planar and may be used as lubricants. For example, the compound and polymer of the invention may be used as a lubricant between cartilage.

These and other aspects of the present invention will become evident upon reference to the following detailed description and attached drawing. In addition, reference is made herein to various publications, which are hereby incorporated by reference in their entirety.

BRIEF DESCRIPTION OF THE DRAWINGS

The invention will now be described in relation to the drawings in which.

DETAILED DESCRIPTION OF THE INVENTION

Compounds of the Invention

Figure 1:
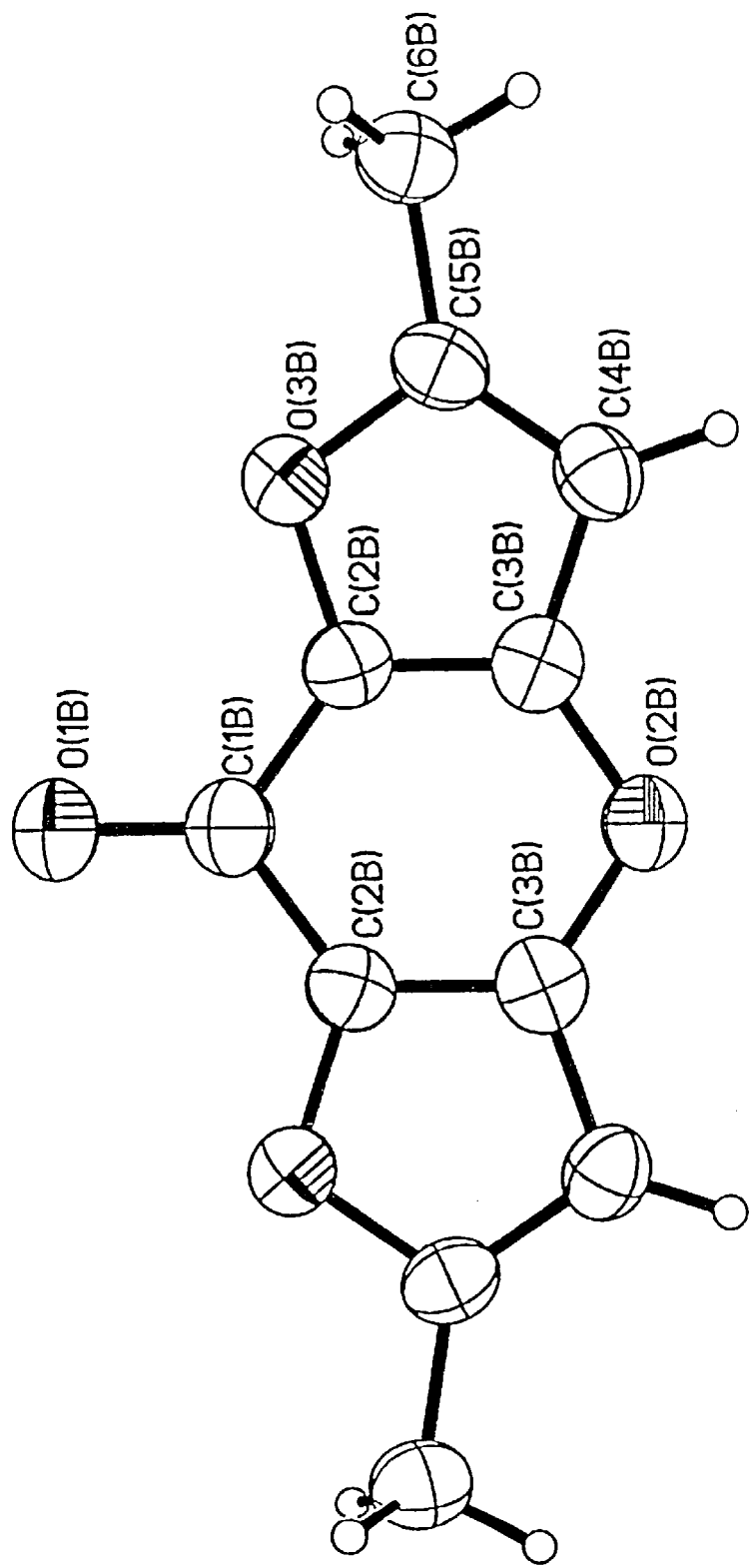
FIG. 1 shows the molecular structure of a compound of the invention determined from single crystal x-ray diffraction.

The invention relates to a compound of the formula I wherein $R^1$ and $R^2$ are the same or different and represent hydrogen, alkyl, alkenyl, alkynyl, alkoxy, hydroxyl, thiol, amino, halogen, carboxylic acid or esters or thioesters thereof, amide, azide, imide, imine, imidazole, acetal, nitrile, nitro, sulfate, sulfonic or sulfinic acid or esters thereof, phosphate or phosphonate acids or esters thereof, silyl, sulfoxide, sulfone, oxime, phosphonate, cycloalkyl, unsaturated monocyclic hydrocarbons, aryl, and aryloxy, and salts and optically active and racemic forms of a compound of the formula I.

Hereinabove and in the following the term "alkyl", alone or in combination, refers to a branched or linear hydrocarbon radical, typically containing from 1 through 20 carbon atoms, preferably 1 through 6. Typical alkyl groups include but are not limited to methyl, ethyl, 1-propyl, 2-propyl, 1-butyl, 2-butyl, tert-butyl, pentyl, hexyl, and the like.

The term "alkenyl", alone or in combination, refers to an unsaturated branched or linear group typically having from 2 to 20 carbon atoms and at least one double bond. Examples of such groups include but are not limited to ethenyl, 1-propenyl, 2-propenyl, 1-butenyl. 1,3-butadiene, hexenyl, pentenyl, and the like.

The term "alkynyl", alone or in combination, refers to an unsaturated branched or linear group having 2 to 20 carbon atoms and at least one triple bond. Examples of such groups include but are not limited to ethynyl, 1-propynyl, 2-propynyl, 1-butynyl, 2-butynyl, 1-pentynyl, and the like.

The term "alkoxy" alone or in combination, refers to an alkyl or cycloalkyl linked to the parent molecular moiety through an oxygen atom. The term "aryloxy" refers to an aryl linked to the parent molecular moiety through an oxygen atom. Examples of alkoxy groups are methoxy, ethoxy, propoxy, vinyloxy, allyloxy, butoxy, pentoxy, hexoxy, cyclopentoxy, and cyclohexoxy. Examples of aryloxy groups are phenyloxy, O-benzyl i.e. benzyloxy, O-p-nitrobenzyl and O-p-methyl-benzyl, 4-nitrophenyloxy, 4-chlorophenyloxy, and the like.

The term "halo" or "halogen", alone or in combination, refers to a member of the family fluorine, chlorine, bromine, or iodine.

The term "amino", alone or in combination, refers to a chemical functional group where a nitrogen atom (N) is bonded to three substituents being any combination of hydrogen, alkyl, alkenyl, or alkynyl, with the general chemical formula $-NR^7R^8$ where $R^7$ and $R^8$ can be any combination of hydrogen, alkyl, alkenyl, or alkynyl. Optionally one substituent on the nitrogen atom can be a hydroxyl group (—OH) to give an amine known as a hydroxylamine. Examples of amino groups are amino ($-NH_2$), methylamine, ethylamine, dimethylamine and hydroxylamine.

A "carboxylic acid" chemical functional group, alone or in combination, has the formula —COOH. Esters of carboxylic acids have the chemical functional group $R^{11}COOR^{12}$ where $R^{11}$ represents the primary skeleton structure of a compound of the formula I and $R^{12}$ is alkyl, alkenyl, or alkynyl. Preferred carboxylic acid esters ($-CO_2R^{12}$) include methyl esters ($-CO_2CH_3$), ethyl esters ($-CO_2CH_2CH_3$), propyl esters ($-CO_2CH_2CH_2CH_3$), allyl esters ($-CO_2CH_2CH=CH_2$), and butyl esters ($-CO_2CH_2CH_2CH_2CH_3$).

Thioesters have the general formula $R^{13}COSR^{14}$ where $R^{13}$ represents the primary skeleton of a compound of the formula I, and $R^{14}$ is an alkyl, alkenyl. Examples of thioesters are analogous to those provided for the carboxylic acid esters presented above.

The term "amides", alone or in combination, refers to a chemical functional group of the formula $R^{15}CONR^{16}R^{17}$ where $R^{15}$ represents the primary skeleton of compounds of the formula I, and $R^{16}$, and $R^{17}$ are any combination of hydrogen, alkyl, alkenyl, or alkynyl. Examples of amide substituents for the compounds of the formula I include: $-CONH_2$, $-CONHCH_3$, $-CON(CH_3)_2$, $-CONHCH_2CH_3$, and $CON(CH_2CH_3)_2$.

Thiol groups (also known as mercaptans) have the general formula —SH. Nitro groups have the general formula $-NO_2$. Azide groups have the general formula $-N_3$.

The term "cycloalkyl" refers to cyclic hydrocarbon groups and includes but is not limited to cyclopropyl, cyclobutyl, cyclopentyl, cyclohexyl, cycloheptyl, and cyclooctyl. The terms "cycloalkenyl" and "cycloalkynyl" refer to unsaturated monocyclic hydrocarbons having one endocyclic double or one triple bond. Compounds of the formula I having more than one such multiple bond are cycloalkadienyl, cycloalkatrienyl, etc. The inclusive term for any cyclic hydrocarbons having any number of such multiple bonds is unsaturated monocyclic hydrocarbons. Examples of unsaturated monocyclic hydrocarbons are cyclohexene, cyclopentadiene, and cyclooctadiene.

The term "aryl", alone or in combination, refers to a monocyclic or polycyclic group, preferably a monocyclic or bicyclic group. An aryl group may optionally be substituted as described herein. Examples of aryl groups and substituted aryl groups are phenyl, benzyl, p-nitrobenzyl, p-methoxybenzyl, biphenyl, and naphthyl.

One or more of $R^1$ and $R^2$ alone or together, which contain available functional groups as described herein, may be substituted with one or more of the following: alkyl, aryl, cycloalkyl, alkenyl, alkynyl, alkoxy, hydroxyl, thiol, an unsaturated monocyclic hydrocarbon, —$SR^9$ wherein $R^9$ is alkyl, cycloalkyl, alkenyl, alkynyl, or unsaturated monocyclic hydrocarbons, thiol, thioaryl, amino, ammonium, halogen, carboxylic acid or ester, ketone, aldehyde, carbonate, carbamate, amide, azide, imide, imine, imidazole, acetal, ketal, nitrile, diazo, nitro, hydrazine, hydrazide, hydrazone, hydroxamic acid, oxime, hydroxylamine, sulfate, sulfonic or sulfinic acid or ester, sulfonamide, phosphate or phosphonate acids or esters, silyl, sulfoxide, sulfone, oxime, guanidino, phosphonate, thioamide, thiocarbamate, thiocyanate, thioketone, thiourea, triazole, cyano, nitrite, urea or xanthate. The term "one or more" used herein preferably refers to from 1 to 3 substituents, most preferably 1 to 2 substituents.

The invention also contemplates compounds of the formula I wherein one or more of the oxygens are replace with N or S, and compounds of the formula I wherein the oxygen, N or S is substituted with one or more of the substituents described herein.

Organic compounds can exist in optically active forms. Such compounds possess the property of being able to rotate the plane of plane-polarised light in either a dextrorotary [prefix (+)] or levorotary [prefix (-)] manner. Typically an optically active compound possesses an asymmetric or stereochiral center such as a tetrahedral carbon atom which is bonded to four different atoms or groups. The four different atoms or groups can be arranged around the asymmetric carbon atom in two ways to give two stereochiral compounds which are structurally related as non-superimposable mirror images of one another. Such compounds are termed stereoisomers or enantiomers. Enantiomers have identical physical and chemical properties except that they rotate the plane of plane-polarised light by an equal amount but in opposite directions. A racemic mixture is a mixture of equal amounts of a pair of enantiomers. Such a mixture does not cause rotation of the plane of plane-polarised light.

The terms "R" and "S" are commonly used in organic chemistry to denote a specific configuration of a stereochiral center. The term "R" or "rectus" refers to that configuration of a stereochiral center with a clockwise relationship of group priorities (highest to second lowest atomic number) when viewed along the bond toward the lowest priority group. The term "S" or "sinister" refers to that configuration of a stereochiral center with a counterclockwise relationship of group priorities (highest to second lowest) when viewed along the bond toward the lowest priority group. The priority of groups is based upon their atomic number (heaviest isotope first). A partial list of priorities and a discussion of stereo-chemistry is contained in the book: The Vocabulary of Organic Chemistry Orchin, et al., John Wiley and Sons Inc., publishers, page 126, which is incorporated herein by reference.

Depending on the radicals $R^1$ and $R^2$, a compound of formula I may exist in, and be isolated in, optically active and racemic forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer. Therefore, the present invention contemplates all optical isomers and racemic forms thereof of compounds of the invention, and the formula of the compound shown herein is intended to encompass all possible optical isomers of the compound so depicted.

The present invention also contemplates salts and esters of the compound of the formula I of the invention. In particular, the present invention includes pharmaceutically acceptable salts. By pharmaceutically acceptable salts is meant those salts which are suitable for use in contact with the tissues of humans and lower animals without undue toxicity, irritation, allergic response and the like, and are commensurate with a reasonable benefit/risk ratio. Pharmaceutically acceptable salts are well known in the art and are described for example, in S. M. Berge, et al., J. Pharmaceutical Sciences, 1977, 66:1–19. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The invention also contemplates a crystal form of a compound of the invention. In an embodiment of the invention a crystal form is contemplated that has a space group $Cmc2_1$.

A compound of the invention may be conjugated to substances to form molecular conjugates. In particular, a compound of the invention may be conjugated to an imaging or therapeutic agent.

A plurality of compounds of the invention may be linked to form a polymer. For example, from 2 to 200 compounds of the invention can be linked to form a polymer.

The invention also contemplates a precursor of a compound of the invention. The following are possible precursors of a compound of the formula I:

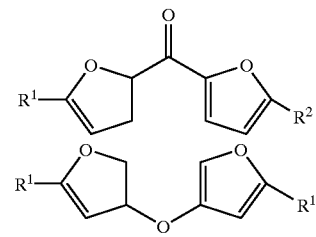

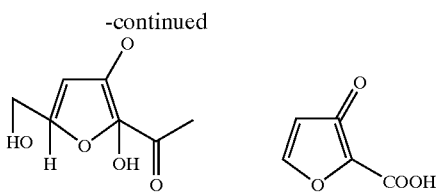

A compound of the invention may be isolated from cartilage by acid hydrolysis, and fractionation on a liquid chromatography system. In particular, cartilage may be hydrolyzed with HCl (e.g. 6N), resuspended in the mobile phase, and separated by HPLC.

Salts, isomers, and crystals of compounds of the invention may be prepared from the isolated compounds by conventional methods.

A compound of the invention may also be produced by a synthetic route.

Table 1 sets out the characteristics of a preferred compound of the invention. The preferred compound has the following molecular formula: $C_{11}H_8O_4$ and a molecular weight of $204.17 \pm 0.15$. A crystal form of the compound has a $Cmc2_1$ space group and an orthorhombic unit cell symmetry.

Diagnostic Methods

The present invention provides a method of diagnosis of a condition involving modifications in cartilage, intervertebral discs, and/or cartilagenous metaplasia and neoplasia of tissues in a subject comprising detecting a compound of the invention or a precursor thereof, in a biological sample from the subject. The invention also provides a method of monitoring progress of a condition involving modifications in cartilage and/or an intervertebral disc in a subject or of monitoring efficacy of treatment of such a condition, comprising periodically testing a sample from the subject for the presence of a compound of the invention, or a precursor thereof. The invention still further provides a method of monitoring normal growth and development in a subject. In these methods the quantitated levels are compared to levels obtained for other samples from the subject, or control individuals.

In an embodiment of the invention, the methods of the invention are used to diagnose or monitor a cartilagenous condition. Examples of such conditions include a degenerative joint disease associated with clinical disabilities, age-related degeneration of cartilage that occurs independent of structural disintegration or with mild structural aberrations, or joint trauma. Degenerative joint disease includes any form of arthritis or arthropathy, more preferably selected from the group consisting of rheumatoid arthritis, juvenile arthritis, osteoarthritis, psoriatic arthritis, hemophilic arthritis, suppurative arthritis, chondrocalcinosis, chondromalacia patella, avascular necrosis of bone, ochronosis, neuropathic arthropathy, immobilization, gout, Crohn's arthropathy, arthritis associated with spondylitis, tenosynovitis and bursitis associated with infectious agents, and disc degeneration. Other conditions include neoplasms (including primary benign and malignant neoplasms of cartilage, neoplasms in which cartilage is one component, cartilage-containing hamartomas, tumors that simulate cartilagenous neoplasms, conditions with chondromatous metaplasia and neoplasia, cartilagenous remnants presenting as tumors, and syndromes with cartilage-containing neoplasms, metastatic neoplasms).

It will be appreciated that it would be useful to have a diagnostic test which recognizes a subject's condition as an irregularity n cartilage, even without defining the precise syndrome. Additional tests within the sphere of known arthritic and bone diseases can be performed once it is established that this is the subset of problems from which diagnosis will emerge.

The presence of a compound of the invention or a precursor thereof may be detected in a variety of biological samples including biological fluids and tissues such as urine, plasma, synovial fluid, cerebral spinal fluid (CSF), and serum, and cell culture medium. A sample may be treated as described herein to isolate a purified preparation containing a compound of the invention. The amount of compound in the preparation may be quantitated using techniques known in the art. For example, if a preparation is obtained by acid hydrolysis the compound may be detected using fluorescent techniques.

A compound of the invention or a precursor thereof may be detected in a sample or purified preparation using a substance which directly or indirectly interacts with the compound or a precursor thereof. For example, antibodies specific for a compound of the invention may be used to diagnose and monitor a condition involving modifications in cartilage, articular cartilage containing tissues such as intervertebral disc, trachea, and sternum, and/or cartilagenous metaplasia and neoplasia of tissues. A method of the invention using antibodies may utilize Countercurrent Immuno-Electrophoresis (CIEP), Radioimmunoassays, Radioimmunoprecipitations, and Enzyme-Linked Immuno-Sorbent Assays (ELISA), Dot Blot assays, Inhibition or Competition assays and sandwich assays (see U.S. Pat. Nos. 4,376,110 and 4,486,530; see also Antibodies: A Laboratory Manual, Supra).

Antibodies used in the methods of the invention include monoclonal antibodies, polyclonal antibodies, antibody fragments (e.g., Fab, and $F(ab')_2$) and recombinantly produced binding partners. Polyclonal antibodies may be readily generated by one of ordinary skill in the art from a variety of warm-blooded animals such as horses, cows, various fowl, rabbits, mice, or rats. Monoclonal antibodies may also be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Binding partners may be constructed utilizing recombinant DNA techniques to incorporate the variable regions of a gene which encodes a specifically binding antibody (See Bird et al., Science 242:423–426, 1988).

Antibodies specific for a compound of the invention or a precursor thereof may be labelled using conventional methods with various enzymes, fluorescent materials, luminescent materials and radioactive materials. Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive materials include radioactive phosphorous $^{32}P$, iodine $I^{125}$, $I^{131}$ or tritium.

An antibody specific for a compound of the invention or a precursor thereof may also be indirectly labelled with a ligand binding partner. For example, the antibodies may be conjugated to one partner of a ligand binding pair. Representative examples of ligand binding pairs include avidin-biotin, and riboflavin—riboflavin binding protein. Preferably the antibodies are biotinylated. Methods for conjugating the antibodies discussed above with the ligand binding partner may be readily accomplished by one of ordinary skill in the art (see Wilchek and Bayer, "The Avidin-Biotin Complex in Bioanalytical Applications," Anal Biochem. 171:1–32, 1988).

The antibodies used in the method of the invention may be insolubilized. For example, the antibodies may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized compound or antibodies may be prepared by reacting the material with a suitable insoluble carrier using known chemical or physical methods, for example, cyanogen bromide coupling.

Indirect methods may also be employed in which a primary antigen-antibody reaction is amplified by the introduction of a second antibody, having specificity for the antibody reactive against the compound of the invention. By way of example, if the antibody having specificity against a compound of the invention is a rabbit IgG antibody, the second antibody may be goat anti-rabbit gamma-globulin labelled with a detectable substance as described herein.

The diagnostic and monitoring applications described herein require that the amount of a compound of the invention or a precursor thereof quantitated in a sample from an individual being tested be compared to levels quantitated for another sample, or an earlier sample from the individual, or levels quantitated for a control sample. Levels for control samples from healthy individuals may be established by prospective and/or retrospective statistical studies. Healthy individuals who have no clinically evident disease or abnormalities may be selected for statistical studies. Diagnosis may be made by finding different levels of a compound of the invention or a precursor thereof compared to a control sample or previous levels quantitated for the same individual.

The methods of the invention can be carried out using a diagnostic kit for quantitating a compound of the invention or a precursor thereof in a sample. The kit may contain an agent that specifically binds to a compound of the invention e.g. antibodies specific for the compound, an agent such as an antibody specific for a compound of the invention coupled to one member of a ligand binding pair e.g. biotin; an enzyme coupled to the other member of the ligand binding pair e.g. streptavidin; and a substrate for the enzyme which forms fluorescent complexes. The kit may contain antibodies specific for a compound of the invention coupled to one member of a ligand binding pair e.g. biotin; an enzyme coupled to the other member of the ligand binding pair e.g. streptavidin; and a substrate for the enzyme which forms fluorescent complexes. The kit may also contain microtiter plate wells, standards, assay diluent, wash buffer, adhesive plate covers, and/or instructions for carrying out a method of the invention using the kit.

Regulation of a Condition Involving Modifications in Cartilage, Intervertebral Discs, and/or Cartilageous Metaplasia and Neoplasia of Tissues in a Subject The invention provides a method of screening for putative therapeutic agents for the prevention and/or treatment of a condition involving modifications in cartilage, intervertebral discs, and/or cartilagenous metaplasia and neoplasia of tissues comprising testing the ability of the putative therapeutic agents to interact with, degrade, or inhibit or stimulate a compound of the invention, or a precursor thereof. Conventional assay methods may be used to identify the putative therapeutic agents. The utility of the compounds and agents of the invention may be confirmed in animal experimental model systems (See for example K. Pritzker, Annals of the Rheumatic Diseases 53:406, 1994; C. Colombo et al. Arthritis and Rheumatism 26:875, 1983; A. Ratcliffe et al., J. Orthopaedic Research, 350, 1992; R. Holmdahl et al, Arthritis and Rheumatism 29:400, 1986; and D. Visco et al, Osteoarthritis and Cartilage 4–9, 1996; for models for osteoarthritis).

Putative therapeutic agents and/or a compound of the invention may be used to regulate a condition involving modifications in cartilage and/or articular cartilage containing tissues such as intervertebral disc, trachea, and sternum, in a subject. In particular, a putative therapeutic agent and/or compound of the invention may be used to regulate a cartilagenous condition (see above for examples of these conditions).

The term "subject" refers to a warm-blooded animal such as a mammal which is afflicted with a particular disease state or condition as described herein. Examples of animals within the scope of the meaning of the term are dogs, cats, rats, mice, horses, bovine cattle, monkeys, sheep, and humans.

The agents, compounds, and polymers of the invention have valuable pharmacological properties and they may be incorporated into pharmaceutical compositions for use in treating the conditions mentioned herein. The agents and/or compounds of the invention may be converted using customary methods into pharmaceutical compositions. The pharmaceutical compositions contain the compounds either alone or together with other active substances. Such pharmaceutical compositions can be for oral, topical, rectal, parenteral, local, inhalant, or intracerebral use. They are therefore in solid or semisolid form, for example pills, tablets, creams, gelatin capsules, capsules, suppositories, soft gelatin capsules, liposomes (see for example, U.S. Pat. Ser. No. 5,376,452), gels, membranes, and tubelets. For parenteral and intracerebral uses, those forms for intramuscular or subcutaneous administration can be used, or forms for infusion or intravenous or intracerebral injection can be used, and can therefore be prepared as solutions of the compounds or as powders of the active compounds to be mixed with one or more pharmaceutically acceptable excipients or diluents, suitable for the aforesaid uses and with an osmolarity which is compatible with the physiological fluids. For local use, those preparations in the form of creams or ointments for topical use or in the form of sprays should be considered; for inhalant uses, preparations in the form of sprays, for example, nose sprays, should be considered.

The pharmaceutical compositions can be prepared by per se known methods for the preparation of pharmaceutically acceptable compositions which can be administered to subjects, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, the compounds in association with one or more pharmaceutically acceptable vehicles or diluents, and contained in buffered solutions with a suitable pH and iso-osmotic with the physiological fluids.

The compounds, agents, and polymers are indicated as therapeutic agents either alone or in conjunction with other therapeutic agents or other forms of therapy. For example, the compounds may be used in combination with anti-inflammatories. In particular, the compounds may be used in combination with non-steroidal and/or steroidal anti-inflammatory agents, growth factors, and enzyme inhibitors. The compounds of the invention may be administered concurrently, separately, or sequentially with other therapeutic agents or therapies.

The amount of active substance administered to a subject will depend on such factors as body weight of the animal to be treated, the particular disease to be treated, the severity of the disease to be treated, the nature of the administration route, the therapy desired, the type of animal and its individual behavior towards the medicine or the nature of its formulation and the time or interval at which it is administered. Where major amounts are administered, it may be advisable to divide these into several administrations over the course of the day, or in a form for a timed release system.

The invention also features a method for delivering a substance to a tissue e.g. cartilage tissue or intervertebral disc, the method includes administering to a subject the substance linked to a compound of the invention. Examples of substances that may be delivered to cartilage tissue or intervertebral disc include imaging or therapeutic agents.

The compound of the invention, and polymers thereof are planar and may be used as lubricants. For example, the compound and polymer of the invention may be used as a lubricant between cartilage.

The present invention will be further understood from the following non-limiting examples:

EXAMPLE 1

Purification of Cartilage Marker-1
Materials and Methods
Experimental Animals

Fully encapsulated bovine metacarpophalangeal joints (n=350, age<two yrs) were obtained from the abattoir (Ryding Regency, Toronto). The joints were dissected within 24 hours of death. Most of the excised articular cartilage was used for cartilage culture experiments and the remaining was used for the purification of CM-1 or for the preparation of CM-1 calibrator. The excised articular cartilage was freeze-dried and stored at −70° C.

Cartilage Hydrolysis and Preparation

The bovine metacarpophalangeal articular cartilage was freeze-dried for at least 24 hours. Eight to ten grams of lyophilized cartilage flakes were placed in a 500 ml pyrex bottle and hydrolysed in a sand bath with 320–400 ml (1 mg: 40 $\mu$l) of 6N HCl for 24 hours at an average temperature of 110° C. The temperature of the sand bath was regulated so that the bottom of the bottle had a temperature of 115° C. and the surface of the solution was 105° C. The hydrolysed cartilage was cooled and further evaporated in a round pyrex flask (Fischer Scientific) using a rotoevaporator. The dried hydrolysate was resuspended in a total volume of 25 ml of 50% HPLC grade methanol (Caledon Laboratories) and 50%, of HPLC grade water (Omnisolve from Fischer Scientific). After rigorous vortexing, the black slurry was then filtered through a sterilized, HPLC grade methanol washed 0.22 $\mu$m Gelman filter and aliquoted into 2 ml Hewlett Packard HPLC injection vials.

In an alternate method, ten milligrams of lyphophilized articular cartilage flakes was hydrolysed in a heated vessel (e.g. PicoTag WorkStation) with 200 $\mu$l (1 mg: 20 $\mu$l) of 6N HCl for 6 hours at an average temperature of 110° C. The hydrolysed cartilage was dried overnight using a speed-vac (Savant). The dried hydrolysate was redissolved in the mobile phase used for the subsequent chromatography (e.g. 24% acetonitrile in water/1% HBA). After vortexing, the black slurry was then filtered through a sterilized, HPLC grade methanol washed 0.22 $\mu$m Gelman filter and aliquoted into 2 ml Hewlett Packard HPLC injection vials.

High Pressure Liquid Chromatography Purification of CM-1

The CM-1 separation method involved a total of three cycles of sample injection-peak collection-lyophilization-resuspension stages. The HPLC system consisted of Hewlett Packard HPLC pumps (model 1050), a Hewlett Packard automatic injector (series 1100), a Hewlett Packard Diode Array absorbance detector (model 1050) and a Perkin Elmer fluorescent detector (model LC 240). The following solvents were used: Hydrochloric acid (Sigma), HPLC grade water (Omnisolve from Fischer Scientific), HPLC grade methanol (Caledon Laboratories), and HPLC grade acetonitrile (Caledon Laboratories). The CM-1 peak was collected manually and care was taken to discard the tails of the CM-1 peak to minimize any possible co-eluting and contaminating compound. The three steps of CM-1 HPLC purification were as follows:

Semi Purification of CM-1—Step 1 (30% Acetonitrile)

One ml of the filtered cartilage hydrolysate was injected onto the HPLC semi-preparatory Phenomenex Sphereclone column (250×10 mm, pore size 5 $\mu$m pore size, 2 ODS). The mobile phase comprised of 30% acetonitrile; flow rate was 4 ml/min; back pressure was about 170–190 bars, i.e., 2550 psi; and the retention time (RT) of CM-1 elution peak was 19 min. The fluoresence excitation was 306 nm and emission 395 nm. The UV spectrum was observed at the maximum UV absorbance of 306 nm wavelength. The CM-1 fractions collected from all the sample injections were pooled, evaporated (Fraction A), and resuspended in 50% methanol/50% water.

The control sample was comprised of only 700 ml of 6N HCl. The control was subjected to a similar experimental protocol and conditions as the CM-1. The control sample was hydrolysed at a temperature of 110° C. for 24 hours in the sand bath, lyophilized and resuspended in 15 ml of 50% methanol in HPLC grade water. The control was filtered and injected onto the semi-preparatory sphereclone column. The control sample corresponding to the RT of 19 min was manually collected for a period of 3 minutes, lyophilized and resuspended in 50% methanol and 50% water.

Semi Purification Step—Step 2 (20% Acetonitrile)

The lyophilized fraction A (semi purified CM-1) was resuspended in 5 ml of 50% methanol and 1 ml of the semi pure CM-1 was injected into the Hewlett Packard HPLC system using a new sphereclone semipreparatory C-18 column with the same size and dimensions as that used in step 1. A guard column was not necessary at this stage of the purification. The mobile phase used was 20% acetonitrile to separate any compound that was co-eluting with CM-1 in step 1. The flow rate was four ml/min; back pressure was about 190 bar; and retention time of the CM-1 peak was 41 min. The tail of the peak was again not collected. The CM-1 fractions collected from all the injections were pooled and evaporated (Fraction B).

The control fraction collected in step 1 was processed and injected in the same manner as that of the semi purified CM-1. Control fractions in this step were collected from RT 40 min for ten minutes duration.

Final Purification Step—Step 3 (50% Methanol)

The lyophilized fraction B (from semi-purification step 2) was resuspended in 4 ml of 50% methanol/50% water and 2 ml of the semi pure CM-1 was injected into the Hewlett Packard HPLC system using a sphereclone analytical C-18 column with the same stationary phase and particle size as used in the above two semipurification steps (1 & 2). The mobile phase used was 50% methanol/50% water. The rationale was to change the solvent composition to separate any compound that was co-eluting with CM-1 in steps 1 & 2. The flow rate was 1 ml/min; back pressure of about 190 bar and retention time (RT) of the CM-1 peak was 16 min. The tails of the peak were again not collected. The CM-1 fractions collected from all the injections were pooled, and lyophilized (Fraction C). Control fractions in this step were collected for seven minutes duration from retention time of 16 mins.

The 20 ml flask containing the purified CM-1 was washed with 1 ml of 100% deuterated methanol for six times, i.e., a total volume of 6 ml. The wash containing CM-1 was transferred into a preweighed test tube and dried with nitrogen. A total of 1.37 mg of light yellowish powder of CM-1 (or 6.7 µmoles) was purified from 116.00 gm dry weight of calf metaphalangeal articular cartilage (11.81 µg or 57.89 nmoles of CM-1/gm of dry weight articular cartilage).

Crystallization of Purified Cartilage Marker-1

Purified CM-1 (1.37 mg) was resuspended in 80 µl of 100% deuterated methanol, briefly vortexed and placed in a 3 mm inner diameter tube (Nerelac Glass Ware) which was used to acquire data during nuclear magnetic resonance spectroscopy. The above procedure was further repeated twice making a total volume of 240 µl. The transfer of deuterated methanol was done quickly and carefully to prevent any proton exchange with the environment which could interfere with the nmr data acquisition. The mass spectroscopy and nmr spectroscopy (described below) was done on CM-1 and the control sample. The nmr tube containing CM-1 in solution (5.71 µg/µl) was then placed in the freezer at $-9°$ C. Pale yellow crystals developed within 8–10 days and reached their final size after several additional days. The supernatant was removed and the crystals were analysed by single crystal x-ray diffraction (XRD). From the control sample no crystals were observed when seeded for crystallization for up to a period of one month.

Preparation of A Calibrator For Quantifying Cartilage Marker-1

A calibrator of CM-1 was prepared from 16.62 gm (dry weight) of calf metaphalangeal articular cartilage. CM-1 was isolated and purified using the procedure described above. A total of 0.3 mg of CM-1 was purified giving a yield of 18.05 µg of CM-1/gm of dry weight of calf metaphalangeal articular cartilage. The purified CM-1 powder was then dissolved in 10 ml of 50% methanol/50% water. The measured UV absorbance at maximum 306 nm wavelength was 0.6906 AU. The molar extinction coefficient of CM-1 in 50% methanol solvent is 4698.4/Mol./cm=~4700/Mole/cm (In comparison to Pyridinoline=5700/Mol./cm and deoxypyridinoline=5000/Mol./cm). Since CM-1 is novel and there is no available reference material, a one "unit" of CM-1 was arbitrarily defined as the quantity present within one milliliter of neutral pH water exhibiting a UV-maximum absorbance of 1 absorbance unit at 306 nm. Therefore, one unit=213 nmol. For analytical purpose the pyridinoline, deoxypyridinoline, and CM-1 calibrators were combined to give one external calibrator Discussion During bulk preparation, a yield of 11.81 µg or 57.89 nmoles of CM-1/gm of dry weight of calf metacarpophalangeal articular cartilage was obtained. The CM-1 calibrator preparation yielded 18.05 µg of CM-1/gm of dry weight of calf metacarpophalangeal articular cartilage. The difference in the CM-1 yield of the bulk preparation and calibrator preparation can be attributed to discarding of the collection of CM-1 in the anterior and posterior tail of the peak and slight loss of the CM-1 due to a more exhaustive procedure used in the bulk preparation of CM-1. The CM-1 was crystallized in 100% methanol to yield 100% pure CM-1 (slightly yellowish crystal). Crystals of CM-1 were grown from a CM-1 solution of 5.71 mg/ml of CM-1 at pH 7.0 at $-9°$ C. in deuterated water.

A control sample (6 N HCl without the cartilage) was also prepared using a similar method. No crystals were formed when seeded for crystallization for up to a period of one month.

EXAMPLE 2

Moldeular Structure and Atomic Identificaiton of Cartilage Marker-1

I. Mass Spectrometry

Mass spectrometry of CM-1 was analyzed from two different Mass spectrometry laboratories: Mass Spectrometry Laboratory, Carbohydrate Research Centre (University of Toronto) and the Mass Spectrometry Laboratory, Chemistry Department (University of Toronto). Mass spectrometry experiments were done on 5 different preparations of CM-1. The control sample consisted of equal volumes of 6N HCl (without cartilage) as was used in the preparation of CM-1. The conditions for preparing the control sample were the same as those used for the preparation of CM-1. Two experiments were done: Ion Spray Mass Spectrometry (ISMS) and Electron Impact Mass Spectrometry (EIMS).

Ion Spray Mass Spectrometry (ISMS)

Material And Methods

The ISMS experiments were carried out on the Perkin Elmer/Sciex (Concord, Ontario) API-III triple quadrupole mass spectrometer. The mobile phase consisted of a solution of 50% acetonitrile and 50% water, 1 mM ammonium acetate, and 0.1% acetic acid. The mobile phase was pumped at a flow rate of 0.020 mL/min using the LKB Bromma (Sweden) HPLC pump. The voltage applied to the tip of the ion spray needle was 5.00 kvolts and the voltage applied to the orifice was 80 volts. One to 20 µl of the sample solution was injected into the mass spectrometer. The tandem mass spectrometry (MS/MS) experiment gives information on the structure of the selected parent ion. The sample was injected and ionized on a needle probe i.e. where ions were formed. MS/MS scans were obtained by mass selecting a parent ion that was observed in the normal mass spectrometry scan into the second quadrupole. The pressure of the collision gas (argon) in the second quadrupole determined the degree of fragmentation, and was set such that the collision gas target (CGT) had a value of 200 to 250 (UNITS).

Results

Mass spectrometry clearly shows a striking difference between the two collected fractions i.e. CM-1 versus control. The $[(H_2O)_4MeOH]H^+$ fragment originates from the methanol:water solvent (50:50) in which the sample (CM-1 or control) was dissolved. The MW 204 dalton species appeared over a relatively narrow time range as the probe was heated and could be "separated" from the bulk of the impurity in the spectrum.

Electron Impact Mass Spectrometry (EIMS)

Material and Methods

A micromass 70–250S (double focusing) Sector Mass Spectrometer was employed operating at an accelerating voltage of 8 keV. Approximately 0.5 µl of CM-1 in solution (5.71 mg/ml) was applied to the platinum coil of a Direct Chemical Ionization (DCI) probe tip, inserted into the source of the mass spectrometry and rapidly heated at 20 mA/s to desorb the sample as the mass spectrometer was scanned at a rate of ca 1 scan per second. The source temperature was 250 EC and the source pressure was $10^{-6}$ mbar.

To further confirm the structural analysis, high-resolution experiments were conducted on two separate preparations of CM-1 and at two different times. The instrument was operated at 10,000 resolution (10% valley) $2\phi=5.7$ ppm based on 27 measurements of the molecular ion of cholesterol.

Results

The 70 eV Electron Impact (EI) spectrum of CM-1 had the molecular ion of m/z 204.041 daltons as the base peak and few abundant fragment ions, which suggested a low ionization potential, stable structure for the molecular ion, consistent with an aromatic structure. The molecular ion (m/z 204) decomposed through loss of m/z 29 (CHO) to afford m/z 175 ($C_{10}H_7O_3$); a loss of m/z 79 ($C_5H_3O$) to yield m/z 125 ($C_6H_5O_3$) and a fragment of m/z 80 ($C_5H_4O$). All elemental compositions were verified by high-resolution measurement. The species of MW 204 appeared over a relatively narrow time range as the DCI probe was heated and thus could be "separated" from the bulk of the impurity spectra. High-resolution measurements on both the CM-1 preparations at two different times yielded values of 204.0418 amu and 204.0426 amu for the molecular ion. When these values were submitted for possible "fits" for C, H, O (0–4), N(0–2) and P(0–2), the possibility that emerged was $C_{11}H_8O_4$. This identification was also supported by examination of the isotopic distribution of the molecular ion. The fragment at 175.0391 u was identified using the above criteria as $C_{10}H_7O_3$ arising via CHO loss from the appropriate 204. The fragment at 125.0240 was also identified as $C_6H_5O_3$ arising from the loss of $C_5H_3O$ from the respective 204. The fragment at m/z 80.0259 u was identified as $C_5H_4O$. From an examination of the isotopic distribution of the molecular ion, the correct formula for CM-1 appeared to be $C_{11}H_8O_4$. From the data, the molecule was considered as consisting of two portions—125 u and 79 u (which appeared as a protonated fragment at m/z 80). The 79 portion had an aldehyde function which was readily cleaved and had the formula $C_5H_3O$ ($C_5H_4O$ when protonated). The 125 portion had the formula $C_6H_5O_3$ and was thought to have a trihydroxy benzene structure.

Mass Spectrometry Conclusions

Both low resolution and high-resolution mass spectroscopy showed that the parent peak of purified CM-1 molecule has a molecular weight of 204 daltons and possible molecular formula of $C_{11}H_8O_4$.

II. Nuclear Magnetic Resonance Spectroscopy

To elucidate the chemical structure and atomic connectivity of CM-1 in solution the following nuclear magnetic resonance (NMR) spectroscopic experiments were acquired: one-dimensional (1-D) proton ($^1H$) and carbon ($^{13}C$) nmr spectra, and two-dimensional (2-D) Heteronuclear Multiple Quantum Correlation (HMQC) and Heteronuclear Multiple Bond Correlation (HMBC) nmr spectra. The nmr spectra of CM-1 were acquired and analyzed at the NMR laboratory in the Chemistry Department (University of Toronto) using a 500 MHz Varian UNITY nmr spectrometer. They were acquired prior to-and post crystallization of the purified CM-1. A 3 mm closed nmr tube containing 1.37 mg of CM-1 in 240 µl of deuterated methanol (5.71 mg/ml) was placed in the 3 mm Nalorac direct microprobe for analysis. The experiments were run at a temperature of 40° C. unless otherwise specified.

One-Dimensional NMR Spectroscopy

Materials And Methods

The proton ($^1H$) spectrum was recorded at ambient temperature using a single pulse experiment. The 1-D $^1H$ spectrum was of sufficiently high digital resolution and signal to noise ratio that the spin—spin coupling was observable in the nmr spectrum. The spectrum consisted of 16 scans acquired using a 60° pulse and a 0.976 s recycle delay. Another $^1H$ NMR spectrum was repeated with a 20 s repetition time in order to determine the extent of $T_1$ discrimination on the integration of the signals. The $^{13}C$ nmr spectrum was recorded at ambient temperature using a single pulse experiment. It was obtained with 4711 scans, using a 90-degree pulse and a 50 s recycle delay.

Results

The $^1H$ nmr spectrum showed two peaks of interest, one at 2.49 ppm (methyl singlet) and another at 6.63 ppm (olefinic singlet). All $^1H$ chemical shifts were recorded with respect to trimetylsulfonyl (TMS). The singlet peaks indicate that these functional groups neighbour no other protons. The methanol and water proton peaks were the prominent peaks in the spectrum. The other weak resonances observed originated from impurities.

A typical $^{13}C$ NMR spectrum of CM-1 showed six singlets. This took into account the restraining condition that the molecular weight of this molecule is 204 dalton (as determined by the MS data). It was concluded that there is a high degree of symmetry in the CM-1 molecule. This symmetry simplified the $^{13}C$ NMR spectrum to six signals. The presence of only singlets indicated that all carbons attached to protons were isolated from each other. Peak assignment was performed in standard $^{13}C$ chemical shifts. There were three resonances apparent in the aromatic region of the spectrum, 156 ppm, 158.3 ppm and 161.3 ppm with a relative ratio of 2:1:2. The other singlets were observed at 14.5 ppm (methyl carbon), 100.4 ppm (olefinic carbon) and 139.2 ppm.

Two-Dimensional Spectroscopy

Material And Methods

The HMQC and HMBC experiments were recorded using the Nalorac 3 mm indirect microprobe. A 2-D decoupled HMQC spectrum was run in the phase sensitive mode, with a $^{13}C$ spectral window of 20120 Hz and a $^1H$ spectral window of 4620 Hz. The experiments were done at ambient temperature (20° C.). A 1024 data point was acquired pre scan with a 1s recycle delay. The 2D nmr spectrum consisted of 70 time increments with 1024 scans per time increment (1D spectrum). During the acquisition GARP $^{13}C$ decoupling was applied and a BIRD nulling long relaxation delay of 0.3 s was used. The heteronuclear experiments were recorded essentially as described by Dayi and Wagner.

Results

The 2-D HMQC showed two carbon-proton attached peaks. The proton singlet at 2.49 ppm (methyl singlet) correlated to the carbon at 14.4 ppm whereas the proton singlet at 6.63 ppm correlated to the carbon at 100.5 ppm. The HMBC experiment confirmed the presence of six $^{13}C$ atoms as seen in 1-D $^{13}C$ spectrum.

NMR Spectroscopy Conclusions

The $^{13}C$ nmr spectrum confirmed that both the methyl carbons (14.5 ppm) and methine carbon are isolated from other protons. The $^{13}C$ singlet at 100.4 ppm is an olefinic carbon with an attached proton and the $^{13}C$ singlet at 161 ppm is assigned to the carbon in the aromatic ring directly connected to the methyl group. The $^{13}C$ singlets at 156 ppm and 161.3 ppm correspond to the fully conjugated aromatic/olefinic carbons. The 158.3 ppm peak belongs to a carbonyl carbon in the aromatic ring with no attached protons. The $^{13}$C NMR spectrum suggests that the molecule has a very high degree of symmetry since there are two carbons for almost every unique carbon environment, with the exception at 158.5 ppm. In addition both $^1$H and $^{13}$C nmr confirm that there are only two $^1$H environments present, explaining the simplicity of the uncoupled $^{13}$C NMR spectrum.

III. Single Crystal X-ray Diffraction (Crystallography)

The crystal structure of CM-1 was analyzed from the Crystallography Laboratory, Chemistry Department (University of Toronto). The molecular structure and atomic connectivity of CM-1 in a crystalline phase was investigated using Single-Crystal X-ray Diffraction Analysis.

Materials and Methods

A colorless crystal was selected, mounted on a glass fibre, and stabilized by embedding in epoxy. Single x-ray diffraction was observed from a crystal of volume $13.72 \times 10^{-3}$ mm$^3$. Data were collected at room temperature on a Nonius KappaCCD diffractometer using graphite monochromated MoK∀ radiation (8=0.71073 Å). Three hundred and sixty frames of 1° rotation in phi were exposed for 60 seconds each. The first 15 frames of data were used to index the crystal lattice. Indexing, integration, and scaling were carried out using the DENZO package. Lorentz and polarization corrections were carried out but no absorption correction was applied.

The structures were solved and refined using the SHELXTL\PC package (Siemens, Madison, Wis., U.S.). Refinement was by full-matrix least squares on F$^2$ using all data (negative intensities included). The weighting scheme was $w=1/[\phi^2(F_o^2)+(0.0883P)^2]$ where $P=(F_o^2+2F_c^2)/3$. Hydrogen atoms were included in calculated positions and treated as riding atoms.

Results

Structure of CM-1 Molecules in 3-D Crystalline Phase

The crystals diffracted x-rays isotropically to at least 0.8 Δ in resolution. The lattice parameters of the colorless crystals belong to the orthorhombic system. A summary of selected crystallographic data is given in Table 2. From the systematic absences, space group Cmcm or Cmc2$_1$ was assigned to the colourless crystal of CM-1. The structure solution and refinement proved the space group to be the latter, with cell dimensions a=12.87 (1) Å, b=10.809 (1) Å, c=12.972 (1) Å, alpha=90 Å, beta=90 Å and gamma=90 Å (FIG. 1).

Figure 2:
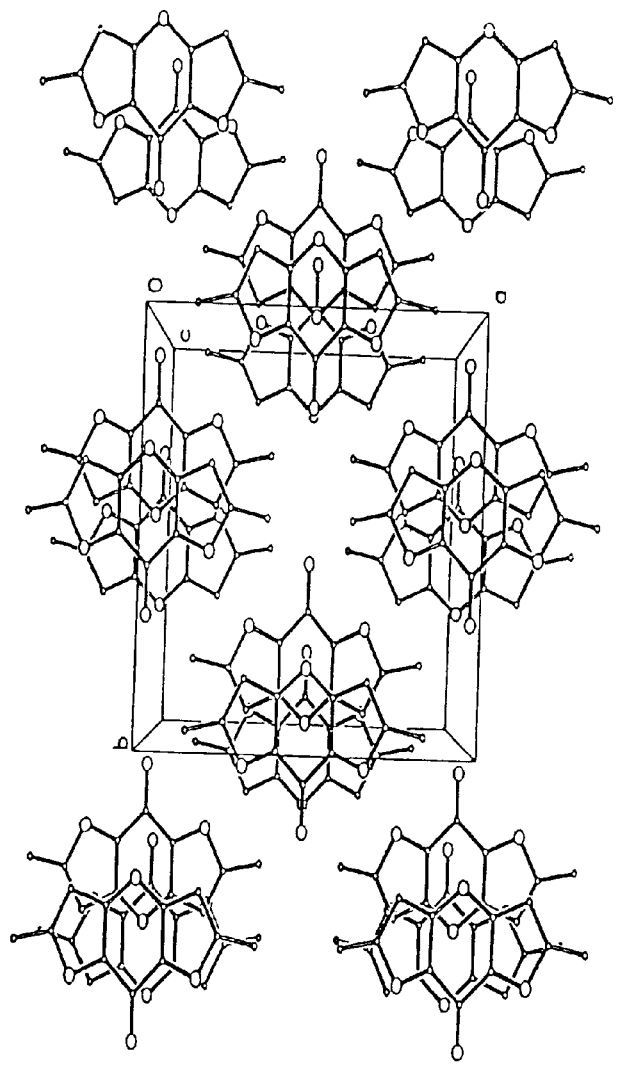
FIG. 2 shows the 3D orientation of a compound of the invention determined from single crystal x-ray diffraction.

The crystal structure has two independent molecules that lie on mirror planes. The mirror plane bisects the molecules through atoms O1A, C1A and O2A for molecule A, and O1B, C1B and O2B for molecule B. The planar molecules stack in the c-direction and align almost parallel to the 0 1 0 plane of the crystal lattice. There is a slight rotation of approximately 6° for molecule A and 4° for molecule B, with respect to the 0 1 0 planes. This rotation (or tilt) was about the long axis of the molecule (FIG. 2). The molecules were rotated by 180° every one half translation of the unit cell, in the c-direction, as a virtue of the 2$_1$ screw axes. An intermolecular distance of 2.41 Å between the C=O group and a methyl hydrogen may be a weak non-bonded interaction but there were no other untoward intermolecular interactions. Weak Vanderwaals forces hold the adjacent molecules together in the crystal.

Molecular Structure of Cartilage Marker-1

Figure 3:
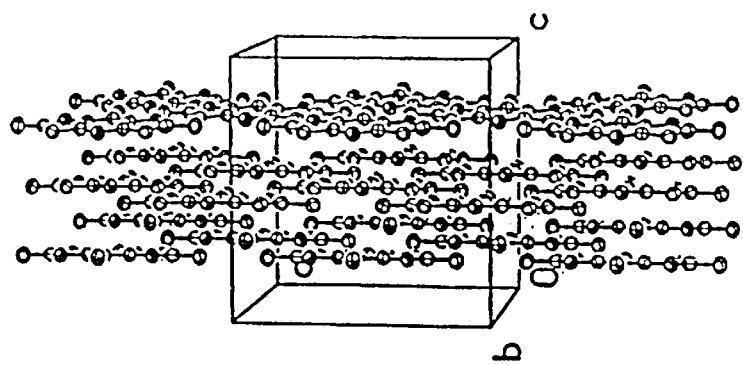
FIG. 3 shows the 3D orientation of a compound of the invention from single crystal x-ray diffraction.
Figure 3:
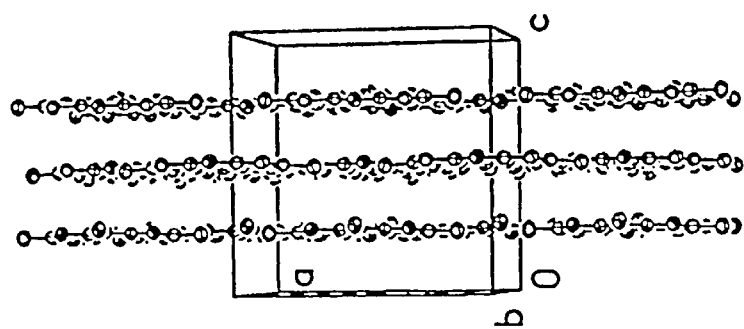

The most striking structural features of CM-1 were the symmetrical, rigid nature of CM-1 and the stacking of the CM-1 molecules. CM-1 is a very stable aromatic molecule consisting of 12 carbon atoms, 8 hydrogen atoms and 4 oxygen atoms. Each molecule has an axis of symmetry (mirror plane) (FIG. 3). Each monomeric unit consists of a methylated furan molecule. The two-methylated furan molecules are arranged symmetrically on the opposite ends of the central pyrone ring. The reactive site of CM-1 is located at the carbonyl—keto region of the central pyrone ring. The methyl group of furan could enable small side-chain movements of the CM-1 molecule. Each molecule is stacked back to back with the carbonyl group alternating between the two opposite sides of the molecule and showed uniformity between various stacks. The arrays of the CM-1 molecules appeared in an orderly fashion.

Analytical Conclusions

The results from the various analytical techniques used to identify CM-1 confirm the molecular structure of CM-1 and its atomic connectivity. Mass spectroscopy data indicates a molecular weight of 204 for CM-1 and a possible molecular formula of $C_{11}H_8O_4$. NMR spectroscopy experiments showed six unique carbon environments and two unique proton environments in CM-1. In conjunction with the MS data, the NMR results indicated a high degree of symmetry in CM-1 and proposed the structure of CM-1 in solution. Since each half of the CM-1 molecule is a mirror image of the other, therefore only six carbon atoms and 4 hydrogen atoms were assigned from the $^1$H and $^{13}$C nmr spectra. The single crystal x-ray diffraction of CM-1 conclusively provided the structure of CM-1 in the solid state which agreed with the NMR data in the solution state. Thus, the solid state structure of CM-1 is also that of CM-1 in the solution state. The molecular structure of CM-1 provided by nmr spectroscopy in solution and x-ray crystallography in crystalline state showed that there was no structural change upon crystallization of CM-1. The molecular structure of CM-1 outlined can thus serve as a useful "fingerprint" for the identification of CM-1.

EXAMPLE 3

A. Hydrolysis of Articular Cartilage for Varying Time Points

Materials and Methods

Fully encapsulated bovine metaphalangeal joints (age<two yrs) were obtained from the abattoir. The joints were dissected within 2–4 hours of death. Approximately 50 mg of dry weight cartilage per test tube were hydrolysed in an oven with 1000 µl of 6N HCl at 110° C for varying time points. Each time point had 3 to 5 replicates. The hydrolysate was lyophilized and dissolved in 1000 µl of mobile phase (1% HFBA and 24% acetonitrile in distilled water). The hydrolysate was briefly vortexed and then filtered through a 0.45 µm pore Gelman filter. An aliquot of 15 µl hydrolysate was applied to the HPLC column. The flow rate was 1.0 ml/minute. Pyridinoline (Pyd), deoxypyridinoline (Dpyd), and CM-1 fluorescence were monitored at an excitation of 295 nm and emission of 395 nm. The peaks of interest were quantitated using the pooled Metra Pyd/Dpyd HPLC calibrator and the CM-1 calibrator prepared in house (1 Unit=213 nmol/ml).

Results and Discussion

The CM-1 yield was maximum at 6–7 hrs of hydrolysis (703±28 pmol/mg of cartilage). However a slight decrease in CM-1 yield to 574±20 pmol/mg of cartilage was observed at 48 hrs of hydrolysis. This indicates that prolonged hydrolysis of articular cartilage could result in degradation of CM-1. The optimal time of hydrolysis of articular cartilage to get the best yield of CM-1 is 6 to 7 hours hrs (>90% of CM-1 available in articular cartilage at this time).

The maximum yield of Pyd at 24 hrs (2233±205(SD) pmol/mg of cartilage) corroborates previous reports. Even after 48 and 120 hrs of cartilage hydrolysis, Pyd content (2381±130(SD) pmol/mg and 2373±131 (SD) pmol/mg, respectively) did not significantly change. On the other hand, Dpyd showed a maximum yield at 15 hrs (171±16 pmol/mg dry weight cartilage) and at 48 hrs its value was 125±4 pmol/mg dry weight cartilage.

B. Hydrolysis of Different Amounts of Articular Cartilage

Materials and Methods

Articular cartilage weighing 25, 50, 75 and 100 mg were hydrolyzed with 1000 µl of 6N HCl for 24 hrs at 110° C. Each concentration combination was repeated three times. An aliquot of 30 µl hydrolysate was applied to the HPLC column.

Results and Discussions

The yield of CM-1 per mg of cartilage (130.7±8.84 pmol/mg) was significantly less (by 50%) when 25 mg of cartilage was hydrolyzed with 1000 µl 6N HCl compared to the CM-1 yield (243 to 256 pmol/mg) when 50 to 100 mg of cartilage was hydrolyzed under similar condition. This data shows that the ratio of tissue dry weight to the volume of hydrolyzing agent (6N HCl) plays an important role in determining the yield of CM-1. The optimal ratio of tissue dry weight to volume of HCl is 1 (mg): 20 (µl). At this optimal ratio, yield of CM-1 is maximum. It is possible that at this ratio there is equilibrium between CM-1 formation and CM-1 degradation. However, when the volume of HCl is in excess, the equilibrium between CM-1 formation and CM-1 degradation appears to shift such that the yield of CM-1 is decreased.

C. Rehydrolysis of Purified Cartilage Marker-1 For 24 Hours

Materials and Methods

An aliquot of purified CM-1 was lyophilized. The lyophilized CM-1 was resuspended in 7 ml of 50% HPLC grade methanol. The UV absorption of CM-1 was measured at 306 nm using a Shimatzu Spectrophotometer. The methanol was evaporated and CM-1 was rehydrolysed for 48 hrs in 6N HCl at 110° C. CM-1 was then lyophilized and resuspended in 7 ml of 50% HPLC grade methanol. The UV absorption of CM-1 was measured.

Results and Discussion

The typical UV absorption spectrum of CM-1 consisted of a larger peak at 306 nm with UV absorption value (AU) of 1.884 and a smaller peak at 278 nm of 1.00. However, after treatment of the purified CM-1 with 500 µl 6N HCl, the typical UV absorption profile of CM-1 was altered to a profile with three peaks. The UV absorption at 306 nm decreased to 0.469 AU (decrease by 75%) and at 276 nm it decreased to 0.4865 AU (decrease by 51%).

The results of the rehydrolysis of purified CM-1 indicate that CM-1 is degraded when treated with 6N HCl at 110° C. Although the aromatic structure of CM-1 is maintained with prolonged hydrolysis, it appears that CM-1 cannot withstand prolonged rehydrolysis. The covalent bonds of the aromatic structure are broken perhaps at the reactive site of the molecule i.e. the keto group of central pyrone ring. This may further result in rearrangement of the molecule and/or further breaking of the weak bonds. This may be due to the absence of steric hinderance (provided by other cartilage macro and micromolecules) which directly exposes CM-1 to the harsh treatment of HCl.

During the hydrolysis of CM-1 the electronegative oxygen atom in the pyrone's carbonyl (C=O) group has a fractional negative charge $\delta^-$ and the carbon has a positive charge $\delta^+$. The protons of HCl (acting as an electrophile) are attracted to the oxygen. This could lead to an intermediate that can accentuate the positive charge on the carbon atom, making it more attractive to a nucleophile, in this case water. This in turn could result in the hydrolysis of C=O bond and hence the instability of CM-1 molecule.

D. Rehydrolysis of Purified Cartilage Marker-1 For Different Time Points

Materials and Methods

100 µl of CM-1 calibrator was lyophilized, resuspended in 3.0 ml of 50% methanol and UV absorbance was measured. Five aliquots of 500 µl each were rehydrolyzed with 1000 µl 6N HCl at 110° C. for 3, 6, 12, 24 and 48 hrs. The rehydrolyzed CM-1 was lyophilized and resuspended in 500 µl of 50% methanol and UV absorbance was measured. Methanol was then evaporated and the samples were resuspended in 500 µl of the mobile phase and injected into the HPLC analytical column. The results of rehydrolysis of CM-1 were compared to the unhydrolyzed CM-1 calibrator.

Results and Discussion

For the interpretation of this data an unhydrolyzed aliquot of CM-1 calibrator was assumed to yield 100% CM-1. A decrease in CM-1 yield to 64% was observed at 3 hrs of CM-1 rehydrolysis and was maintained up to 12 hrs. However, the CM-1 yield decreased to 19% by 24 hrs and further to 4.5% by 48 hrs of CM-1 rehydrolysis. This data suggests that CM-1 is not stable when rehydrolyzed for a prolonged period. This observation may be due to the direct exposure (lack of steric hinderance) of CM-1 molecules to HCl molecules. This could increase the susceptibility of electrophilic attack to CM-1 that in turn may result in the opening of the pyrone ring structure in the center of the CM-1 molecule. The data shows that purified CM-1 is not stable when rehydrolyzed with 6N HCl.

E. Hydrolysis of Articular Cartilage with Varying Concentrations NaOH or HCl

Materials and Methods

Fifty mg of dry weight articular cartilage per test tube were hydrolysed in the oven (110° C.) with 1000 µl of different concentrations of HCl and NaOH for 6 hrs (3 replicates). The hydrolysate was lyophilized and processed as mentioned above.

Results and Discussions

CM-1 and the pyridinium crosslinks are released only by the hydrolysis of articular cartilage with 6N HCl. Hydrolysis of articular cartilage with NaOH did not release CM-1 or pyridinoline crosslinks.

F. Hydrolysis of Articular Cartilage with Acids and Bases

Materials and Methods

Fifty mg of dry weight articular cartilage per test tube were hydrolysed in an oven (110° C.) with 1000 µl of 50% each of acetic acid, nitric acid, sulfuric acid, or ammonium hydroxide for 24 hrs (3 replicates). The hydrolysate was lyophilized and injected onto HPLC analytical column.

Results And Discussion

The CM-1 peak was not generated by acetic acid, nitric acid, sulfuric acid or ammonium hydroxide. This data corroborates other studies showing that HCl hydrolysis is essential for the formation of the CM-1 molecule.

G. Effect of Mobile Phase pH on the Retention Time of Cartilage Marker-1

Materials and Methods

The established method for Pyd, Dpyd and CM-1 was followed using mobile phase (25% acetonitrile, 75% distilled water). The pH of mobile phase was adjusted from 1.0 to 5.0. The retention time of Pyd, Dpyd and CM-1 was noted.

Results and Discussion

When processed cartilage samples were injected on the column with mobile phase of pH ranging from 1 to 5.0, a significant shift (to the left) in the retention time of the pyridinium crosslinks was noted indicating its polar nature. However, there was no significant shift in the retention time of the CM-1 indicating that either it is an amphoteric or nonpolar compound.

II. Requirement of Heptafluorobutyric Acid for Production of Cartilage Marker-1

Materials and Methods

Hydrolyzed cartilage samples were injected (30 µl) onto the analytical column using mobile phase with and without 1% HFBA. The retention time and peak area of Pyd, Dpyd, and CM-1 was noted.

Results and Discussion

HFBA did not have an effect on the retention time or the peak area of CM-1. However, without HFBA the Pyd and Dpyd peaks decreased the peak area of Pyd and Dpyd as well as shifted its RT. HFBA (214 dalton) is an ion pair reagent used in mobile phase for reverse phase HPLC separation of proteins and peptides. The use of ion-pairing reagents greatly enhances the flexibility and resolving power of reverse phase HPLC. However its use did not make any difference to the resolving power of CM-1.

I. Fluorescent and Ultra-violet Light Absorption of Cartilage Marker-1

Materials and Methods

The ultraviolet absorbance maximum of CM-1 was investigated in neutral, aqueous solution, in 0.1 and 6N HCl and 0.1 and 10N NaOH using a Shimatzu Spectrophotometer. The fluoresence of emission of CM-1 at different excition wavelengths was investigated.

Results and Discussion

The ultraviolet absorption spectrum at neutral pH showed absorption maxima at 306 nm (1.13 AU). However, at acidic or basic pH, the intensity of ultraviolet absorptivity of the CM-1 was less than at neutral pH. The UV absorbance at 0.1N HCl and 0.1N NaOH were 0.72 AU and 0.57 AU respectively. Although the absorbance decreased with increased concentration of acid and base compared to aqueous solution, the wavelength at maximum absorption remained the same at 306 nm. With the optimal excitation of CM-1 at 306 nm, the emission was at 358 nm. CM-1 differs from other known fluorescent biological molecules present in articular cartilage namely, Pyd and Dpyd, which has an optimal excitation wavelength at 295 nm and pentosidine at 335 nm.

J. Solubility of Cartilage Marker-1 in Various Solvents

Materials and Methods

The ultraviolet absorbance maxima of CM-1 was investigated in methanol, distilled water, chloroform, hexane, ether and ethanol.

Results and Discussion

CM-1 is highly soluble in water and methanol. CM-1 is insoluble in hexane and chloroform.

K. Effect of Degradative Enzymes in the Yield of Cartilage Marker-1

Materials and Methods

Fifty mg of articular cartilage powder (obtained from Sigma Chemicals) was hydrolyzed with 6N HCL (1 ml) in an oven (110° C.) for 24 hrs either directly or post enzyme digestion. Distilled water (1 ml) was used as a negative (without CM-1) and positive control (with CM-1). The various enzymes used individually were: collagenase, pepsin, protease K, guanidine HCl, and papain. Enzyme digestion of articular cartilage powder was done overnight in a water bath at 37° C. except for the papain digestion which was kept overnight at 65° C. The positive control samples were prepared by adding CM-1 (50 µl of 10 mUnit/ml) to the buffer with the respective enzymes. Each sample was centrifuged for 20 mins and the supernatant was separated from the pellet. The supernatants and pellets were hydrolyzed separately. After HCl hydrolysis, the samples were lyophilized and resuspended in 500 µl of mobile phase and filtered using 0.45 µm pore Gelman filter. Fifty µl of each sample was injected onto the HPLC. The recovery of CM-1 and pyridinoline was investigated.

Results and Discussion

The cartilage samples treated with various enzymes showed varying yields of CM-1 and pyridinoline compared to the cartilage samples that were hydrolyzed directly without using any enzyme. The CM-1 yield obtained without enzyme treatment was considered 100%. The best yield for CM-1 and pyridinoline was obtained with papain digestion, and the poorest yield was obtained from guanidine HCL followed by pepsin. It appears that both guanidine HCl and pepsin have a quenching effect on the fluorescence of CM-1 and pyridinoline.

L. Effect of Storing Cartilage Marker-1 at Room Temperature for Eight Months

Materials and Methods

The UV absorbance of CM-1 calibrator (30 ug/ml of 50% methanol) was measured. An aliquot of CM-1 calibrator was kept on the bench top for nine months, and another aliquot was kept in a storage box in a −70° C. freezer for an equal length of time. The UV absorbance of CM-1 calibrator aliquot was measured after eight months of respective storage procedure.

Results and Discussion

The UV absorbance of CM-1 (0.73 AU) at absorption wavelength of 306 nm when stored in the freezer was similar to that of the reference calibrator (0.69 AU). However the calibrator aliqout which was kept in the room temperature decreased to 0.1718 AU (A decrease of 75%). It appears that either the ambient temperature and/or possibly the room light (versus sunlight) itself caused degradation of CM-1 when kept in room temperature for a prolonged period of time. Pyd and Dpyd are known to be light sensitive. The storage method is very important in maintaining the stability of CM-1.

Assay Optimization Conclusions

Optimization of CM-1 isolation and/or the quantification procedure is dependent upon the adequate recovery of CM-1. The experiments establish a protocol that can maximize the yield of CM-1 from the acid hydrolysate of articular cartilage. With hydrochloric acid and high temperature conditions articular cartilage yielded a chromophore, CM-1, with maximal absorbance at 306 nm. Among the known weak and strong acids such as acetic acid, sulfuric acid, nitric acid, and hydrochloric acid, only HCl yielded CM-1. The use of HCl acid is essential for the production of CM-1. CM-1 is a cartilage specific product of acid hydrolysis. Further, rehydrolysis of purified CM-1 with 6N HCl resulted in the degradation of CM-1. The ratio of tissue dry weight to the volume of 6N HCl should not significantly deviate from 1 (mg): 20 µl. It is also important to store CM-1 calibrator in the freezer to prevent its degradation. Heptafluorobutyric acid is not required in the mobile phase for CM-1 quantitation. When cartilage was digested using various enzymes, CM-1 fluorescence was quenched by guanidine —HCL and pepsin.

EXAMPLE 4

Characterization of the Tissue Specificity of Cartilage Marker-1

While investigating collagen crosslinking and fluorescence in articular cartilage, a unique flourescent peak consistently appeared in articular cartilage but not in other dense connective tissues. In order to explore the derivation of CM-1 in biological tissue samples and to validate CM-1 as a cartilage marker, the tissue specificity of CM-1 was investigated. The evaluation of disease activity and cartilage injury in the patients with osteoarthritis, rheumatoid arthritis, chondromalacia patella or osteochondritis requires a reliable biochemical marker. Although several markers are currently used to evaluate the presence of disease, only a few markers specify the stage (severity level) of the disease.

Materials and Methods

Tissue samples obtained from various sources (human autopsy and various animals) were frozen and kept at −40° C. For CM-1 quantification, the samples were lyophilized, weighed, and then hydrolyzed with 1000 $\mu$l of 6N HCl for 24 hours at 110° C. on a sand bath. The hydrolysate was lyophilized, dissolved in 1000 $\mu$l of mobile phase (24% acetonitrile, 1% HFBA and 75% distilled water), briefly vortexed and filtered with 0.45 $\mu$m—pore Gelman filter. An aliquot of 30 $\mu$l hydrolysate was applied to the HPLC analytical column attached to a Hewlett Packard HPLC system. The C-18 column (Phenomenex Spherisorb 5 $\mu$m ODS 2) was protected by a guard cartridge. The flow rate was 1.0 ml/minute. CM-1 flourescence was monitored with a Perkin Elmer Fluorescence detector at 295 nm excitation and 395 nm emission. All sample peaks were quantitated using a CM-1 calibrator that was prepared as described above. The detection limit of CM-1 in the various tissues is 1.74 ng or 8.5 pmol per $\mu$l of sample solution injected.

Results and Discussion

Human Specimens

Human samples were obtained from post-mortem. Synovial fluid samples were obtained either from knee joint effusion from patients or autopsy samples. Due to difficulty in obtaining immature human samples, only one three day human tissue samples was analyzed for the presence of CM-1.

Tissues

Most of the tissues examined from the 3 day human sample detected the presence of CM-1. Articular cartilage (525 pmol/mg tissue) and sternum (295 pmol/mg tissue) showed significant amounts of CM-1. However in adult human tissue samples only articular cartilage, vertebral disc, and trachea showed the presence of CM-1. The amount of CM-1 present in adult articular cartilage (200±15 pmol; 65±14 years) was 2.6 fold less than that present in the three day tissue. CM-1 content was lower in the superficial-middle layers (70±21 pmol), compared to both the middle-deep layers (143±34 pmol) and entire thickness (151±41 pmol) of old articular cartilage. CM-1 was also detected in the acid hydrolyzed articular cartilage containing tissues such as vertebral disc, sternum, and trachea. CM-1 was not detected in non-cartilagenous tissue samples (ligament, tendon, meniscus, bone, esophagus, stomach, intestine, brain, heart, aorta, lungs, muscle, adipose tissue, liver, and kidney).

Body Fluids

CM-1 was not detected in serum, plasma, or urine. Direct analysis of synovial fluid samples, without the acid hydrolysis, failed to reveal any measurable CM-1 compound. CM-1 was higher in synovial fluid of patients with knee joint disease (9±2 pmol) compared to normal value (<3 pmol). Chromatographic prophiles of CM-1 synovial fluid showed that CM-1 eluted at 22 minutes.

Osteoarthritic (OA) Cartilage

Overall Wilcoxon test showed a significant difference (p=0.0007) in CM-1 values between normal and OA cartilage. Statistical analysis showed a significant difference between mild OA and moderate OA (p=0.02) or severe OA (p=0.002). Within the OA group a trend of decreased CM-1 value was noted with the progression of OA. CM-1 was not detected in fibrillated cartilage samples.

Bovine Samples

Tissues

Bovine tissue samples were obtained from the abattoir. CM-1 was detected from calf metacarpophalangeal joint cartilage (362±48 pmol/mg of dry weight cartilage) and intervertebral disc (24.3±4 pmol/mg dry weight). CM-1 was not present in calf ligament, tendon, bone, ocular lens, cornea, and elastic cartilage. A significant difference was noted between the superficial-middle (129±52) and middle-deep layers (448±63) (paired T-test, p=0.008) as well as superficial-middle layer and entire cartilage thickness (p=0.02). There was no significant difference between middle-deep and entire cartilage thickness (p=0.36).

Synovial Fluid and Vitrous Humor

Synovial fluid was collected from the calf metacarpophalangeal joint. CM-1 was detected from 11 (4.54±0.7 pmol/$\mu$l of synovial fluid) out of a total of 13 joints. Examination of the vitrous humor did not detect the synovial fluid.

Lapine Samples

Approximately an 18 fold difference in the CM-1 content of young (6 weeks) versus adult (48 weeks) rabbit knee joint articular cartilage was shown. On the other hand the Pyd and Dpyd content increased 4 fold between young and old cartilage. The amount of CM-1 decreased with increasing age in lapine articular cartilage from an average of 185±40 (<2 weeks) to 27±3 (48 weeks) pmol/mg of dry weight cartilage. CM-1 was present in small amounts in ligament, tendon, meniscus, or bone of ≦10 weeks lapine. CM-1 was not present from the same tissues in 48 week old lapine.

Lamprey Specimens

The sea lamprey is a vertebrate with an entirely cartilaginous skeleton consisting of noncollagenous elastin like proteins. The cartilage morphology is similar to that of elastic cartilage of higher vertebrates. The major connective tissue component of lamprey annular cartilage is Lamprin, an insoluble non-collagen and non-elastin protein. CM-1 was absent from the Lamprey articular cartilage (n=5) examined. This indicates that CM-1 is not present in cartilage samples that do not have the proteoglycans.

Conclusions

CM-1 is a cartilage specific compound which is present in articular cartilage and articular cartilage containing tissues such as trachea, sternum, and intervertebral disc in human (both knee replacement and autopsy samples) and animal samples. In the intervetebral disc the bovine nucleus pulposus has galactosaminoglycan-rich and KS-rich PG monomers. The bovine nasal cartilage has chondroitin sulfate rich PG monomers. Examination of the origin of CM-1 within the cartilage thickness in calf and human samples shows that it is most abundant in the deep lamina and least in the superficial lamina. CM-1 concentration increases from the superficial to deep lamina of articular cartilage. This result correlates with our finding that CM-1 is a product of acid hydrolysis of the carbohydrate moiety of articular cartilage. Proteoglycan also increases from the superficial to the deep cartilage lamina.

The results show that CM-1 is more abundant in young compared to old cartilage. Further, the presence of CM-1 in practically all tissues examined from young human and animal samples indicates that CM-1 is a marker for growth, development, and/or tissue differentiation.

CM-1 was detected in small amounts in the synovial fluid samples of bovine metaphalangeal, and rabbit and human knee joints. However, its presence was not detected in urine samples. Furthermore, the synovial fluid samples were analyzed prior to and post hydrolysis with 6 N HCl. Direct analysis of synovial fluid samples, without the acid hydrolysis, failed to reveal any measurable CM-1. The fluorescent peak of CM-1 could be identified only in the hydrolyzed synovial fluid sample.

CM-1 content decreased in articular cartilage with the progression of osteoarthritis. Further, its level appears to increase in knee joint synovial fluid of patients with arthropathy. CM-1 could be a marker of cartilage catabolism that can be detected in cartilage and synovial fluid with disease progression. CM-1 in synovial fluid of patients has the potential as a diagnostic and prognostic biochemical marker in joint diseases involving articular cartilage degradation.

EXAMPLE 5

Investigation of the Presence of CM-1 in Biological Compounds

The molecular fraction of articular cartilage from which CM-1 is derived was investigated.

A. Isolation and Analysis of Collagen

Material and Methods

Pure type II collagen and type I collagen were obtained from Sigma chemicals. Type II collagen was also extracted from articular cartilage (cartilage excised from bovine metacarpophalangeal joints and cartilage powder from Sigma Chemical) and rat tail tendon. Cartilage samples were digested with pepsin twice for 48 hrs each at 4° C. as described previously. An aliquot from the pepsin digested fraction was analyzed for the presence of CM-1. Pure samples of type I and type II collagens obtained from various sources were hydrolyzed using 6N HCl at 24° C. in an oven (110° C). The hydrolysate was lyophilized and dissolved in 1000 µl of mobile phase (1% HFBA and 24% acetonitrile in distilled water). The hydrolysate was briefly vortexed and then filtered through 0.45 µm pore Gelman filter. An aliquot of 30 µl hydrolysate was applied to the HPLC column. The flow rate was 1.0 ml/minute. Pyridinium and CM-1 fluorescence was monitored at an excitation of 295 nm and emission of 395 nm.

Results and Discussion

CM-1 was absent from all collagen type II (n=6) and collagen type I (n=4) samples. This indicates that CM-1 is derived from another cartilage molecule. Type I or type II collagens do not produce CM-1 upon acid hydrolysis.

B. Amino Acid Analysis

Materials and Methods

The possibility of a peptide constitutent of CM-1 molecule was investigated by using the pico tag system (UV absorption detector) and Waters HPLC system. A purified sample of CM-1 was also sent for amino acid and peptide sequence analysis to the Biotechnology Service Centre at the Banting and Best Institute.

Results and Discussion

Amino acid analysis using the pico tag system (UV absorption detector) did not show the presence of any known amino acids. Therefore, CM-1 is either a non-protein compound, a carbohydrate, or crosslinking protein which could be detected only with a fluorescent detector.

C. Analysis of Proteoglycans

Material and Methods

Cartilage powder was treated with 4M guanidine HCl in 50 mM sodium acetate, pH 5.8 containing 0.1 M 6-aminohexanoic acid, 10 mM EDTA, 50 mM benzamidine HCl and 5 mM N-ethylmaleimide for 24 hours at 4° C. The proteoglycans were precipitated by addition of three volumes of cold ethanol. The pellets were collected by centrifugation at 14,000 rpm for 30 mins, washed three times with 70% ethanol. The HPLC analysis for CM-1 was done according to the method described herein.

Results and Discussion

CM-1 was detected from the guanidine HCl extract of proteoglycans indicating that it could be a breakdown product of the soluble carbohydrate moiety of cartilage. However, when articular cartilage was directly hydrolyzed i.e. without the extensive extraction process, the CM-1 yield was much greater than guanidine HCl treated cartilage suggesting that guanidine HCl has a quenching effect on the yield of CM-1.

D. Analysis of Proteoglycans

Material and Methods

Proteoglycan monomer (porcine nasal cartilage), proteoglycan aggregate (source—porcine nasal cartilage) and glycosaminoglycan (porcine nasal cartilage) were obtained from a collaborator. Chondroitin sulfate C (shark cartilage) chondroitin sulfate A (bovine trachea), keratan sulfate (bovine cornea), hyaluronic acid (human umbilical cord), and sodium hyaluronate were purchased from Sigma chemicals. Proteoglycans, both aggregates and monomer, as well as various types of glycosaminoglycans (GAG) such as chondroitin sulphate A and C, keratan sulphate, and hyaluronic acid were analyzed for the presence of CM-1 using the developed protocol. For comparison unhydrolyzed samples of the above mentioned molecules were also processed for HPLC analysis.

Results and Discussion

CM-1 was present in varying amounts in the purified proteoglycan components such as the proteoglycan monomer, proteoglycan aggregate, glycosaminoglycans, and chondroitin sulfate. Due to variable sources and purification techniques used to purify the molecules, the component of proteoglycan in which CM-1 is present in the highest concentration was not confirmed. Unhydrolyzed samples of the same purified proteoglycan components did not show the presence of CM-1. Thus, CM-1 is associated with the carbohydrate fraction of articular cartilage and CM-1 is a product of HCl hydrolysis.

E. Investigation of CM-1 in Known Fluorescent Amino Acids

Material and Methods

The fluorescent amino acids tryptophan, tyrosine, and phenylalanine (10 mg/ml each) were lyophilized, hydrolyzed (300 µl of 6 N HCl for 24 hr at 110° C.), resuspended in the mobile phase, and injected on C18 column.

Results and Discussion

CM-1 was not detected in tryptophan, tyrosine, and phenylalanine samples. This data confirmed that CM-1 is not derived from known fluorescent amino acid.

F. Effect of Exogenous Ascorbic Acid on the Production of CM-1

Material and Methods

Articular cartilage (50 mg) was hydrolyzed with 0.1 mg and 10 mg of ascorbic acid (Sigma Chemicals) following the protocol described herein. The control samples composed of articular cartilage alone i.e. without ascorbic acid, and ascorbic acid alone without the presence of articular cartilage. Each combination of the experiment was repeated three times.

Results and Discussion

Hydrolysis of ascorbic acid alone did not produce CM-1. When exogenous ascorbic acid was added to a cartilage sample a quenching effect was noted reducing the yield of CM-1 5% when 0.1 mg of ascorbic acid was added, and to 95% when 10 mg of ascorbic acid was added.

Conclusions

CM-1 was absent from all the collagen type II (n=6) and collagen type I (n=4) samples that were processed. CM-1 was present in the proteoglycan components of articular cartilage namely proteoglycan monomer, proteoglycan aggregate, glycosaminoglycans and chondroitin sulfate. Guanidine hydrochloride and ascorbic acid have a quenching effect on the production of CM-1.

EXAMPLE 6

Investigation of Cartilage Marker-1 in Cartilagenous Cultures (Rabbit and Bovine)

The cartilage culture system developed by Boyle et al (Osteoarthritis and Cartilage 1995 3:117) was used to investigate the presence of CM-1, pyridinium crosslinks, and macromolecular content in reconstituted articular cartilage. The advantage of using this culture system is that the chondrocytes maintain their phenotypic expression when cultured on teflon filters. Further the cartilagenous matrix showed that the chondrocyte morphology and macromolecules synthesis was similar to that observed in vivo.

I. Rabbit Cartilage Cultures

Material and Methods

In-Vitro Cartilage Culture

Articular cartilage was excised from rabbit knee joints (femoral condyles, tibial plateau and patella) from very young white New Zealand rabbits (aged 1–2 weeks, weight 145–160 gm) and mature white New Zealand male rabbits (aged 10 weeks, weight 2 Kg.). Chondrocytes were isolated by sequential enzymatic digestion using protease followed by collagenase. Teflon filter inserts (Millicell $CM^R$, Millipore Corp., Bedford, Mass., USA) were placed into the wells of the 24 well culture dish, coated with type II collagen (0.5 mg/ml in 0.1N $CH_3COOH$), dried overnight, and UV sterilized for 30 mins. The cells were maintained in Ham's F12 medium with 5% rabbit serum and plated on the teflon inserts at a density of $1.5 \times 10^6/cm^2$. From day 7 onwards, the cells were supplemented with the medium containing 20% rabbit serum and 50 $\mu$g/ml ascorbic acid (added fresh at all times) on every alternate day. The cells were grown at 37° C., 100% humidity and 5% $CO_2$. The cartilage cultures were harvested at fixed time points i.e. day 6, 14, 21, 35, 56, 77, and 98 and stored at −20° C. till the analysis day.

Histochemistry and Morphology

The cartilage cultures with filter inserts were immediately fixed with 10% formalin, paraffin embedded and 5 $\mu$m thick sections were stained with haematoxylin and eosin (to study cellularity), toluidine blue (to stain the sulphated proteoglycans) and picrosirius red (to stain collagen). The cartilage thickness measurements were obtained from a Leitz dialux 22 microscope with a MTI-65 video camera, Hipad digitizing tablet and mouse, a camera lucida and the Bioquant Bone Morphometry program (R & M Biometrics). A low power objective lens (×6.3) was used and the system magnification factor of ×74.4 was determined by calibrating with a 2 mm length stage micrometer. Cartilage thickness was measured extending from the articular surface to the teflon insert. Ten measurements were taken from each slide. Two slides represented each time point per culture group and a total of three culture groups.

Electron Microscopy (EM)

The cartilage cultures were prefixed in 0.2M phosphate buffer glutaraldehyde (2%) and postfixed in 0.2M phosphate buffer glutaraldehyde with 1% osmium tetroxide. The cartilage blocks were washed in buffer, dehydrated in graded strengths of ethanol, infiltrated with polyethyleneoxide, and finally embedded in spur. Thin sections were stained with uranyl acetate and lead citrate. The EM processing and scanning were processed by the Electron Microscopy Department at Mount Sinai Hospital.

Water Content

The weight of cartilage cultures was measured before and after lyophilization overnight. The difference between the wet weight and dry weight of the cultures was used to determine the percent water content of the cartilage cultures. The dry weight of the teflon filter alone was subtracted from the dry weight of the cartilaginous matrix in order to obtain the exact dry weight.

Collagen Content

The cultures were divested with 20 $\mu$g papain/ml buffer (20 mM ammonium acetate, 1 mM EDTA and 2 mM DTT) for 36 hrs. A 20 $\mu$l or 30 $\mu$l aliquot of the sample was lyophilized and then hydrolyzed by a vapour phase/liquid phase reaction using 6 N HCl containing 1% phenol for 22 hours at 110° C. After hydrolysis, the excess HCl was removed from the reacton vial under vacuum and the hydrosylates were redried (methanol:water:triethylamine in ratio of 2:2:1). The sample was then derivitized (methanol:water:triethylamine:phenylisothiocyanate in ratio of 7:1:1:1) for 30 min at room temperature. The derivatizing solution was removed under vacuum and sample was redried to remove any traces of PITC. The sample was resuspended in sample diluent (200 to 500 $\mu$l) and injected on a Waters reverse phase high performance liquid chromatography (HPLC) system at 38° C. column temperature. The total amino acid and hydroxyproline composition of the sample was determined using the Waters Pico-Tag amino acid method. The amino acid concentration was determined by comparison to amino acid standards obtained from Beckman (Beckman System 7300/6300) to which was added an equal volume of hydroxyproline standard. The total collagen content was estimated by multiplying the values for hydroxyproline by 10. The Proline/hydroxyproline ratios were also calculated.

Proteoglycan Content

The amount of proteoglycan (from the papain digest aliquot) was estimated by measuring sulfated glycosaminoglycan content using the dimethylmethylene blue (DMMB) dye binding assay (Farndale, RW et al, Biochim Biophys Acta 1986, 883:173; Goldberg R L and Kolibas L M, Connect Tissue Res 1990: 24:265). Chondroitin sulfate (Sigma Chemicals, St. Louise, Mo.) was used to generate a standard curve. Colourmetric assays at UV absorbance 525 nm were performed in Titertek 96 well plates and read by Titertek multiscan MCC/340.

DNA Content

The DNA content of the culture samples was determined from an aliquot of papain digested cultures. The samples were reacted with Hoescht dye 33258 and the DNA quantitated fluorometrically with emission wavelength of 365 nm and excitation wavelength of 458 nm. Calf thymus DNA was used as the standard.

Pyridinoline, Deoxypyridinoline and CM-1 Content

Reconstituted cartilage was hydrolyzed with 500 $\mu$l of 6N HCl for 24 hours at 110° C. in an oven. The hydrolysate was dissolved in 300 $\mu$l of mobile phase comprising 24% acetonitrile, 1% HFBA, and 75% distilled water. The hydrolysate was vortexed and filtered with 0.45 $\mu$m—pore Gelman filter. An aliquot of 30 $\mu$l hydrolysate sample was applied to the analytical HPLC column (A Phenomenex Spherisorb 5 $\mu$m ODS2 column protected by a Brownlee C18 guard cartridge). The flow rate was 1.0 ml/minute. Pyd, Dpyd, and CM-1 fluorescence was monitored with a Perkin Elmer Fluorescence detector at 295 nm excitation and 395 nm emission. An external calibrator comprising a mixture of Pyd and Dpyd (purchased from Metra Biosystems) and in house CM-1 calibrator was used to generate a standard curve.

Results
Morphology and Histochemistry

The chondrocytes plated as a monolayer had synthesized extracellular matrix that was evident from its multilayered structure by day 6. With increasing age of the cultures more matrix surrounded the chondrocytes. By day 21 changes in chondrocyte morphology could be visualized. The chondrocytes towards the superficial lamina were mostly elongated and flattened and those adjacent to the filters were bigger and round. Toluidine blue staining intensity reflected lower proteoglycan concentration towards the superficial lamina compared to the deep lamina. Picro-sirius red stained sections were examined under a polarized light microscope. Presence of collagen was evident by day 14. Cartilage collagen architecture, similar to in vivo articular cartilage, was seen by day 21 and more so by day 35. The collagens were oriented parallel to the surface in the superficial lamina and perpendicular to the teflon filter in the deep lamina. Collagen nests were also seen surrounding the chondrocytes by day 35. The cartilage thickness values varied slightly from one culture group to another. However the thickness value increased with time (measured up to 56 days) in all the culture groups.

Electron Microscopy

Electron micrographs of the tissue cultures confirmed the presence and architecture of collagen within the superficial and deep lamina as well as in the territorial and interterritorial domains. The collagen toward the superficial lamina aligned parallel to the surface and was perpendicular to the filter in the deep lamina. The nest appearance of collagen in the territorial region is prominent by day 35.

Water Content

The dry weight of the reconstituted cartilage increased up to day 56 and reached a plateau thereafter. The percent water content of the cartilagenous tissue from day 14 to day 98 (n=55; range=71 to 87) is 80±1 (mean±SEM). The cartilage water content in vitro corroborated with the content in vivo. The plausible reason for 60%±6 water content in day 6 cultures (n=6) could be attributed to the quick drying of the thin cartilage. As a consequence the recorded wet weight was less than the actual value.

Collagen Content

The hydroxyproline content forms approximately 10% of the total collagen content. Therefore hydroxyproline content was multiplied by a factor of 10 to estimate the collagen content in the cartilage cultures. The result from young rabbit chondrocyte culture is described herein. The collagen content increased linearly from day 6 (15 $\mu$g±5) to day 35 (197±10 $\mu$g). When the collagen content was standardized per mg of cartilage, the collagen content for day 21 (104 $\mu$g±16 per mg of cartilage) and day 35 (108 $\mu$g±10 per mg of cartilage) were similar. Collagen hydroxylation using the OH-PRO/PRO ratio showed a trend of increased hydroxylation with culture age. The total protein content of the cartilage cultures increased from 162 $\mu$g±16 at day 6 to 409 $\mu$g±8 at day 35.

Proteoglycan Content

The glycosaminoglycan content in the cartilage matrix of the cultures showed a linear increase from 8 $\mu$g±1 at day 6 to 152 $\mu$g±5 at day 35.

DNA Content

Analysis of DNA content within each culture group remained the same when examined i.e., Day 6 up to Day 35. However, a slight variability in DNA content was noted between the culture groups. Results were obtained from five culture groups and three filters from each group (N=15). The DNA content of each cartilage culture group showed that either there was no cellular proliferative activity or an equilibrium existed between the rate of DNA synthesis and degradation (DNA turnover).

Pyridinoline, Deoxypyridinoline and CM-1 Content

The cartilage culture belonging to both young and old rabbit chondrocyte sources increased in dry weight from day 6 to day 56 showing close weight values. The CM-1 content was first noted at day 21 for both young (0.7 pmol/mg of cartilage) and old (1 pmol/mg of cartilage).

There was an increase in CM-1 area from day 35 to day 98. Cultures were analyzed soon after harvesting. When the cultures were analyzed two years later, an underestimation of the exact CM-1 content in the cartilage cultures seemed to occur. There are two plausible explanations leading to the underestimation of CM-1 in the cultures. First, the time duration between harvesting the cultures and actual analysis could decrease the yield of CM-1. Secondly, the optimal ratio of tissue dry weight to volume of HCl is 1 (mg):20 ($\mu$l). This ratio was determined at a later time point when the cartilage cultures were already processed for crosslink and CM-1 analysis. The cartilage cultures were hydrolyzed at a ratio of 1 (mg):125 ($\mu$l) or more. At this hydrolyzing ratio, CM-1 yield is reduced to almost 99% due to degradation of CM-1 in excess of HCl. This could also explain the large SEM observed at day 56 in old cultures.

Both Pyd and Dpyd content increased from day 6 to day 56 in the young and old cartilage cultures. Although the Pyd and Dpyd content of young cultures were higher than old cultures at day 14, 21 and 35, their levels were comparable at day 6 (young=39 pmol; old=16 pmol/cartilage mg) and day 56 (young=259 pmol and old=238 pmol/cartilage mg).

Discussion

The Boyle et al. cartilage culture system enables the chondrocytes plated on teflon filter inserts to reconstitute and maintain cartilaginous extracellular matrix. The advantage of this cartilage culture system is that the chondrocytes maintain their phenotype and they do not dedifferentiate.

The chondrocytes synthesize extracellular matrix that was evident from its multilayered structure by day 6. With increasing age of the cultures more matrix surrounded the chondrocytes. By day 21 the chondrocyte morphology was similar to that seen in vivo. The chondrocytes towards the superficial zone were mostly elongated and flattened and those adjacent to the filters were bigger and round. Toluidine blue staining intensity reflected lower proteoglycan concentration towards the superficial lamina compared to the deep lamina. Picro-sirius red stained sections were examined under polarized light microscope. Presence of collagen was evident by day 14. The day 35 culture extracellular matrix showed "Benninghoff's gothic arch" organization of collagen fibres which were similar to that seen in vivo. Collagen fibres were oriented parallel to the surface in the superficial zone and perpendicular to the teflon filter in the deep zone. Collagen nest was observed around the chondrocyte by day 35.

During the time period studied (up to 35 days), an increase in cartilage thickness, glycosaminoglycan and collagen content was observed. The glycosaminoglycan content of the cultures showed a linear increase from day 6 up to day 35. The amount of collagen in the cartilage culture at a given time point was determined from the hydroxyproline content. A linear increase in the collagen content was noted up to day 35. An increase in the degree of collagen proline hydroxylation was observed as indicated by hydroxyproline to proline ratio.

The state of chemical maturation and mechanical stability of collagen may be related to the formation of intermolecular covalent crosslinks in connective tissues namely pyridinoline (Pyd) and deoxypyridinoline (Dpyd). During collagen degradation Pyd and Dpyd are released from the extracellular matrix into the joint. In the cartilage matrix, the concentration of these pyridinium crosslinks increases during early postnatal life. The experiments described herein were performed to examine whether young and mature bovine articular chondrocytes cultured on teflon filters synthesized collagen which are able to form mature crosslinks, and whether the de novo synthesized crosslinks varied as a function of the age of the chondrocytes. Mature collagen specific pyridinium crosslinks were detected in the reconstituted cartilage at day 21. The increase in Pyd crosslink was most rapid between days 21 and 35 in young cultures and days 35 and 56 in mature cultures.

Although CM-1 was detected in the culture system, its amount is not accurately reflected because CM-1 degraded when excessive volumes of HCl were used. Secondly, an exogenous supply of ascorbic acid may have also contributed to decreased levels of detected CM-1 since it has a quenching effect on the production of CM-1. The most plausible explanation is the time interval between harvesting the cultures and its analysis since those cultures analyzed immediately gave good yield of CM-1.

II. Bovine Cartilage Cultures
Material and Methods

Articular cartilage was excised separately from the superficial-middle (SM) or middle-deep (MD) layers of calf metaphalangeal joint using a sterile technique as described by Boyle et al. The cartilage slices were placed in a petri dish containing Ham's F12 and 1% antibiotics in HAT. Chondrocytes were isolated from the SM and MD extracellular matrix by sequential enzymatic digestion using proteinase (0.5%, 1 hour, 37° C.), washed three times with Ham's F12 medium and finally digested with collagenase A (0.1%, overnight, 37° C.). Teflon filter inserts (Millicell CMR, Millipore Corp., Bedford, Mass., USA) were placed into the wells of the 24 well culture dish, coated with type II collagen (0.5 mg/ml of 0.1N acetic acid), dried overnight and UV sterilized for 30 mins. The filter inserts were washed thoroughly with Ham's F12 before plating the cells. The isolated SM and MD chondrocytes were washed extensively and resuspended in Ham's F12 with 5% fetal bovine serum (FBS) and plated on the teflon inserts at a density of $3.0 \times 10^6/cm^2$. The cells were supplemented with the medium containing 20% FBS and 100 µg/ml ascorbic acid (added fresh at all times) from day 7 onwards every alternate working day. Some cartilage filter cultures were treated with 10 ng/ml interleukin-1β (Il-1β, human recombinant, Sigma) for 7 days (three changes of the Ham's F12 with 20% FBS and Il-1β) prior to harvesting. The chondrocytes were grown at 37° C., 100% humidity and 5% $CO_2$. The chondrocyte cultures were harvested at fixed time points i.e. day 21, 35, and 56 and stored at −20° C. till the analysis day.

The untreated (controls) and Il-1β-treated SM and MD cartilage cultures were analyzed for cartilage thickness and collagen, proteoglycan, pyridinoline, deoxypyridinoline, and CM-1 content as described herein.

Results
Histochemistry and Morphology

The thickness of the cartilage cultured from the SM and MD chondrocytes increased from Day 21 to 35. Beyond day 35, a slight increase in cartilage thickness was noted in both the groups (SM and MD). The cartilage reconstituted from the chondrocytes of the SM layer was thinner than that reconstituted from the DM layer for the same time point. Furthermore, the Il-1β treated cultures had thinner cartilage compared to the untreated controls for both SM and MD groups.

Proteoglycan Content

The glycosaminoglycan (GAG) content of the SM and MD cartilage cultures increased from day 21 to day 56. However, the GAG content of the MD group at the time points studied was greater than those of the corresponding time points of the SM group. The GAG content of both SM and DM groups decreased when treated with Il-1β for a period of 7 days (three media change) prior to harvesting at the given time point.

Collagen Content

The collagen content of the SM and MD cartilage cultures increased from day 21 to day 56. The collagen content from SM and MD group was similar at the time points studied. The collagen content of both SM and DM groups decreased when cultures were treated with Il-1β for a period of 7 days (three media change) in particular on day 56.

Pyridinoline, Deoxypyridinoline and CM-1 Content

The CM-1 in these cultures was not detected in the cultures because the cultures were hydrolyzed at the ratio of 1 mg cartilage:200 µl HCl. The optimal ratio of tissue dry weight to volume of HCl is 1 (mg):20 (µl). Beyond this established optimal hydrolysis ratio CM-1 was shown to degrade. At the hydrolysis ratio used above 100% of CM-1 is degraded. Futhermore, the addition of exogenous ascorbic (0.1 mg/ml) could have some quenching effect (5% decrease on 50 mg cartilage sample) on the production of CM-1. Alternatively, the two years duration between harvesting the cultures and analyzing them could have played an important role in the degradation of CM-1. CM-1 is derived from a proteoglycan component of articular cartilage which has a short half life.

The crosslinks Pyd and Dpyd increased in SM and MD cultures. A decrease in the Pyd and Dpyd content of Il-1β treated cultures was noted at day 35 and more so at day 56. In general the MD chondrocyte secretes a matrix which has more crosslinks than that secreted by the SM chondrocytes.

Conclusions

Both the rabbit and bovine chondrocytes which synthesized cartilagenous matrix in vitro showed the presence of collagen and glycosaminoglycan. The synthesized collagen formed mature collagen crosslinks namely pyridinoline and deoxypyridinoline. The GAG, collagen, and crosslink content was affected when the cultures were treated with interleukin-1β. CM-1 was not detected in the cultures under the prevailing experimental conditions.

Having illustrated and described the principles of the invention in a preferred embodiment, it should be appreciated to those skilled in the art that the invention can be modified in arrangement and detail without departure from such principles. All modifications coming within the scope of the following claims are claimed.

All publications, patents and patent applications referred to herein are incorporated by reference in their entirety to the same extent as if each individual publication, patent or patent application was specifically and individually indicated to be incorporated by reference in its entirety.

TABLE 1

Physical And Chemical Characterization of CM-1.

| S.No. | METHODOLOGY | S.No. | Features | Characteristics |
|---|---|---|---|---|
| A. | Fluoresence Spectroscopy | 1. | Excitation | 295 nm |
| | | 2. | Emission | 395 nm |
| | | 3. | Mobile Phase | 24% AcN |
| | | 4. | Retention Time | 20 minutes |
| B. | Absorption Spectroscopy | 1. | Solvent | 50% MeOH |
| | (UV Spectroscopy) | 2. | Maximum UV Absorbance | 306 nm |
| | | 3. | Molar extinction coefficient | 4698/(Mole/L)/cm |
| C. | Mass Spectroscopy | 1. | Molecular Weight | 204.04 Daltons |
| | | 2. | Molecular Formula | $C_{11}H_8O_4$ |
| | | 3. | Empirical Formula | $C_{11}H_8O_4$ |
| D. | Nuclear Magnetic Resonance | 1. | Proton Spectroscopy | # of $^1H$ = 8 |
| | Spectroscopy | 2. | Carbon Spectroscopy | # of $^{13}C$ = 11 |
| | | 3. | HMQC | 2 $^1H$ groups attached to 2 $^{13}C$ |
| | | 4. | HMBS | 2 $^1H$ & 6 $^{13}C$ environments |
| E. | Single Crystal X-ray Diffraction | 1. | Empirical Formula | $C_{11}H_8O_4$ |
| | (Crystallography) | 2. | Molecular Weight | 204.17 Daltons |
| | | 3. | Crystal size | orthorhombic |
| | | 4. | Percentage Composition | C (64.71%); H (3.92%); O (31.37%) |

TABLE 2

Summary of Crystal Data, Details of Intensity Collection and Least-Squares Refinement Parameters Of $C_{11}H_8O_4$.

| | |
|---|---|
| empirical formula | $C_{11}H_8O_4$ |
| $M_r$ | 204.17 |
| crystal size, mm | 0.26 × 0.24 × 0.22 |
| crystal class | orthorhombic |
| space group | $Cmc2_1$ |
| temperature, K | 123.0(1)K |
| a, Å | 12.870(1) |
| b, Å | 10.809(1) |
| c, Å | 12.972(1) |
| V, Å$^3$ | 1804.6(3) |
| Z | 8 |
| $D_{calc}$ g cm$^{-3}$ | 1.503 |
| $\mu$(MoK∀), cm$^{-1}$ | 1.16 |
| F(000) | 848 |
| range 2 collected, ° | 2.46 to 26.45 |
| independent reflections | 1897 |
| No. observed data [I > 2Φ(I)] | 1373 |
| $R_1$ [I > 2Φ(I)] | 0.0504 |
| $wR_2$ (all data) | 0.1346 |
| goodness of fit | 0.971 |
| parameters refined | 148 |
| maximum peak in final )F map, eÅ$^{-3}$ | 0.259 |

We claim:

1. A difuro-8-pyrone of the formula I

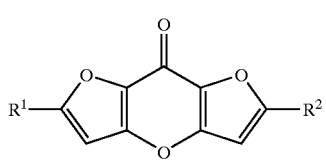

wherein $R^1$ and $R^2$ are methyl, and salts and optically active and racemic forms of a compound of the formula I.

2. A crystal form of a compound as claimed in claim 1, wherein the crystal is of space group $Cmc2_1$.

* * * * *